(12) United States Patent
Sakai et al.

(10) Patent No.: US 7,792,352 B2
(45) Date of Patent: *Sep. 7, 2010

(54) METHOD AND APPARATUS FOR INSPECTING PATTERN DEFECTS

(75) Inventors: Kaoru Sakai, Yokohama (JP); Shunji Maeda, Yokohama (JP); Takafumi Okabe, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/123,160

(22) Filed: May 19, 2008

(65) Prior Publication Data

US 2008/0232674 A1    Sep. 25, 2008

Related U.S. Application Data

(63) Continuation of application No. 10/992,759, filed on Nov. 22, 2004, now Pat. No. 7,388,979.

(30) Foreign Application Priority Data

Nov. 20, 2003    (JP)    ............................. 2003-390655

(51) Int. Cl.
    *G06K 9/00*    (2006.01)
(52) U.S. Cl. ..................... 382/149; 348/87; 348/92; 348/126; 356/237.4; 356/237.5; 382/144; 382/195; 382/218; 382/224
(58) Field of Classification Search ................. 382/145, 382/149, 225, 227, 305
    See application file for complete search history.

(56) References Cited

U.S. PATENT DOCUMENTS

| | | | |
|---|---|---|---|
| 5,515,159 A * | 5/1996 | Sites et al. | ............... 356/237.1 |
| 6,546,308 B2 | 4/2003 | Takagi et al. | |
| 6,650,779 B2 | 11/2003 | Vachtesvanos et al. | |
| 6,661,507 B2 | 12/2003 | Yoda et al. | |
| 6,748,571 B2 * | 6/2004 | Miwa | ............................. 716/4 |
| 6,831,998 B1 * | 12/2004 | Koshishiba et al. | ......... 382/147 |
| 6,879,392 B2 * | 4/2005 | Sakai et al. | ............... 356/237.4 |
| 7,162,073 B1 * | 1/2007 | Akgul et al. | ................ 382/149 |
| 7,171,039 B2 | 1/2007 | Kondo et al. | |
| 7,218,389 B2 | 5/2007 | Uto et al. | |
| 7,229,845 B1 * | 6/2007 | Luu et al. | ..................... 438/16 |
| 7,231,079 B2 | 6/2007 | Okuda et al. | |
| 7,388,979 B2 * | 6/2008 | Sakai et al. | ................. 382/149 |

(Continued)

FOREIGN PATENT DOCUMENTS

JP            03-085742          4/1991

(Continued)

*Primary Examiner*—Gregory M Desire
(74) *Attorney, Agent, or Firm*—Antonelli, Terry, Stout & Kraus, LLP.

(57) ABSTRACT

An apparatus for inspecting pattern defects, the apparatus including: a defect candidate extraction unit configured to perform a defect candidate extraction process by comparing a detected image signal with a reference image signal; and a defect detection unit configured to perform a defect detection process and a defect classification process based on a partial image containing a defect candidate that is extracted by the defect candidate extraction unit, wherein the processes performed by the defect candidate extraction unit and/or the defect detection unit are performed asynchronously with an image acquisition process.

29 Claims, 21 Drawing Sheets

U.S. PATENT DOCUMENTS

| | | |
|---|---|---|
| 2001/0011706 A1 | 8/2001 | Nara et al. |
| 2002/0143719 A1 | 10/2002 | Yoshihara |
| 2002/0154297 A1* | 10/2002 | Noguchi et al. .......... 356/237.3 |
| 2002/0164074 A1* | 11/2002 | Matsugu et al. ............. 382/173 |
| 2003/0060985 A1* | 3/2003 | Mugibayashi et al. ......... 702/35 |
| 2003/0152276 A1* | 8/2003 | Kondo et al. ................ 382/224 |
| 2004/0008880 A1 | 1/2004 | Horie et al. |
| 2004/0028276 A1* | 2/2004 | Okuda et al. ................ 382/224 |
| 2004/0114829 A1* | 6/2004 | LeFeuvre et al. ............ 382/275 |
| 2004/0120569 A1* | 6/2004 | Hung et al. ................. 382/144 |
| 2004/0188609 A1* | 9/2004 | Miyai et al. ................. 250/310 |
| 2004/0228515 A1 | 11/2004 | Okabe et al. |
| 2004/0247171 A1 | 12/2004 | Hashimoto et al. |
| 2005/0147287 A1 | 7/2005 | Sakai et al. |

FOREIGN PATENT DOCUMENTS

| | | |
|---|---|---|
| JP | 08-128976 | 5/1996 |
| JP | 2001-005961 | 1/2001 |
| JP | 2001-077165 | 3/2001 |
| JP | 2001-243905 | 9/2001 |
| JP | 2002-168799 | 6/2002 |
| JP | 2002-310962 | 10/2002 |
| JP | 2003-021605 | 1/2003 |
| JP | 2003-083907 | 3/2003 |
| JP | 2003-271927 | 9/2003 |

* cited by examiner

| DEFECT CANDIDATE NUMBER | CHIP | DETECTION POSITION X | Y | BRIGHTNESS VALUE | AREA | DIMENSION X | DIMENSION Y | POSITIONAL DISPLACEMENT AMOUNT X | Y ... |
|---|---|---|---|---|---|---|---|---|---|
| 1 | 2 | 12000nm | 800nm | 30 | 800nm | 20nm | 40nm | 15nm | 20nm |
| 2 | : | | | | | | | | |

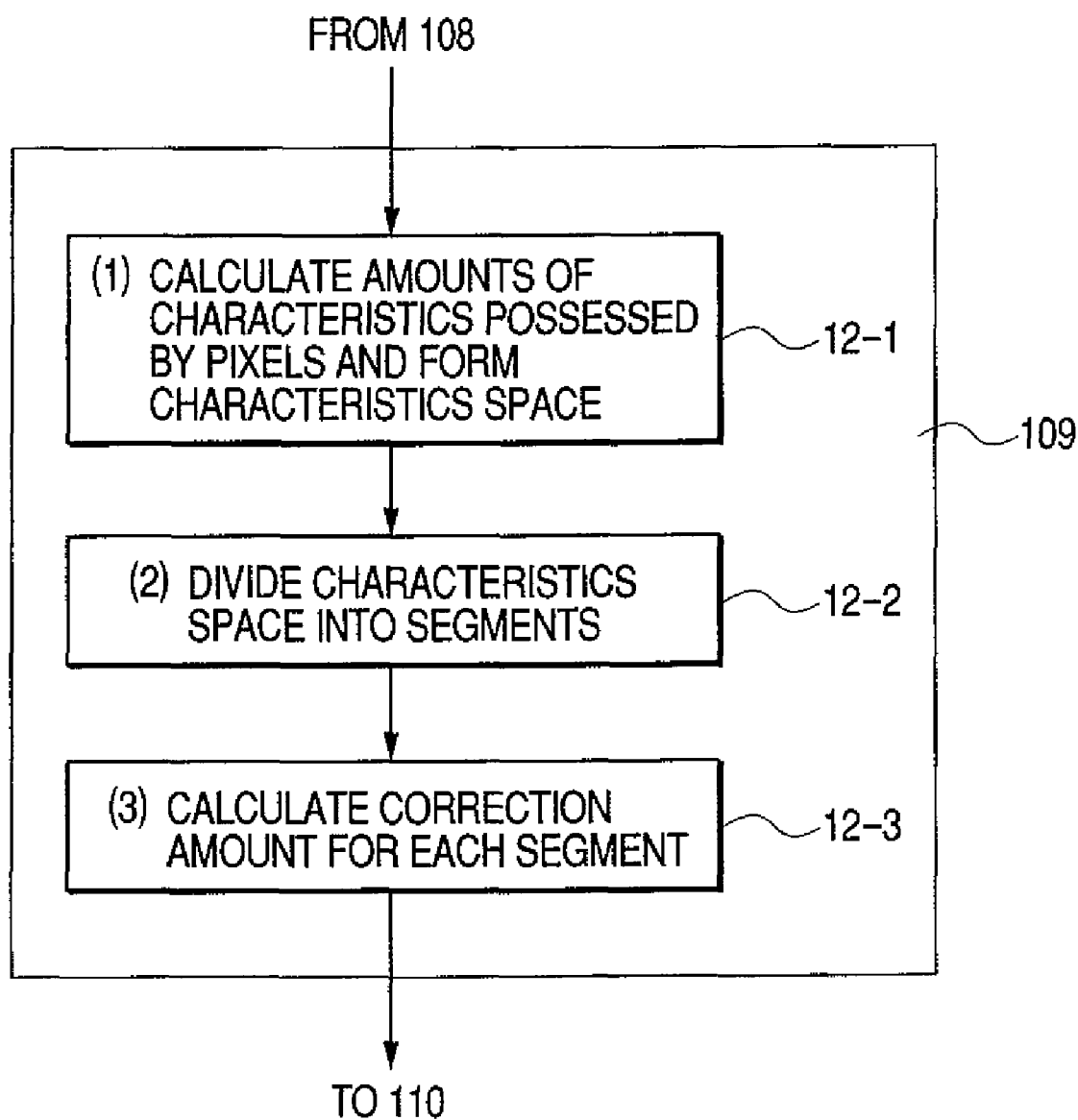

REFERENCE IMAGE

DETECTED IMAGE — DEFECTS

FIG. 14
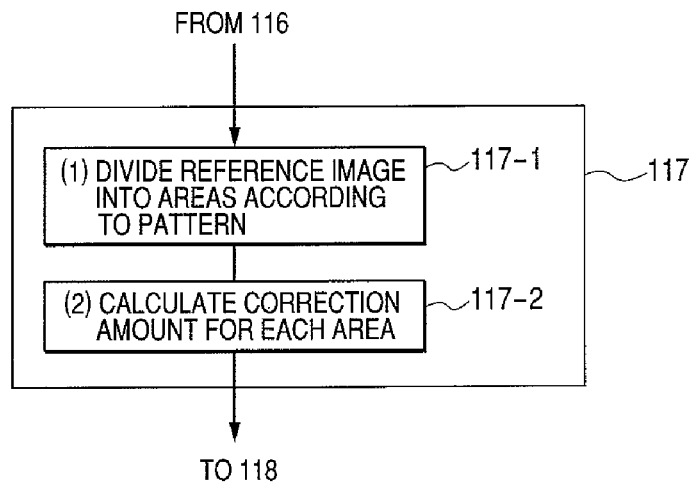
FIG. 15A
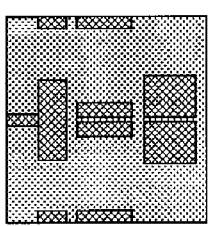
FIG. 15B
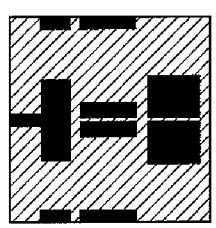 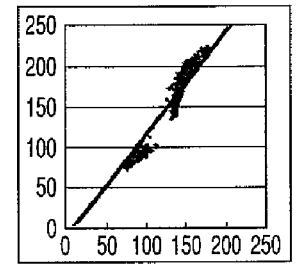
FIG. 15C
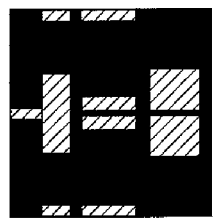 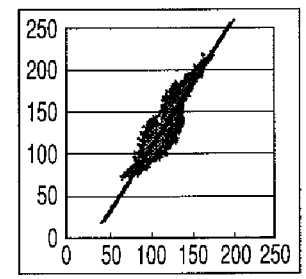

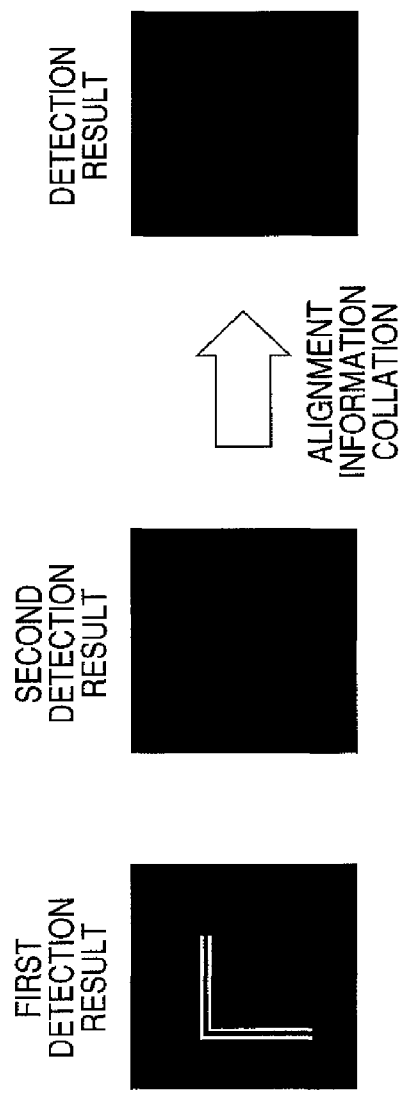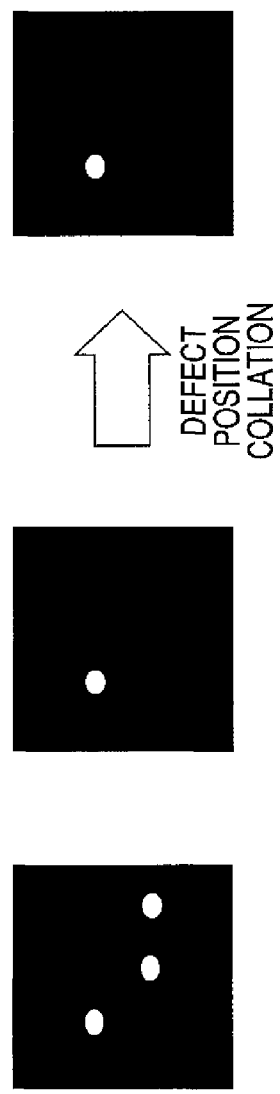

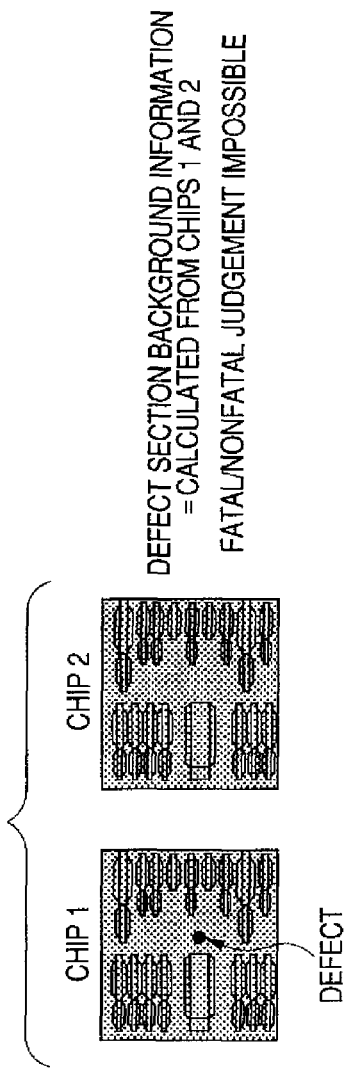
FIG. 17C1
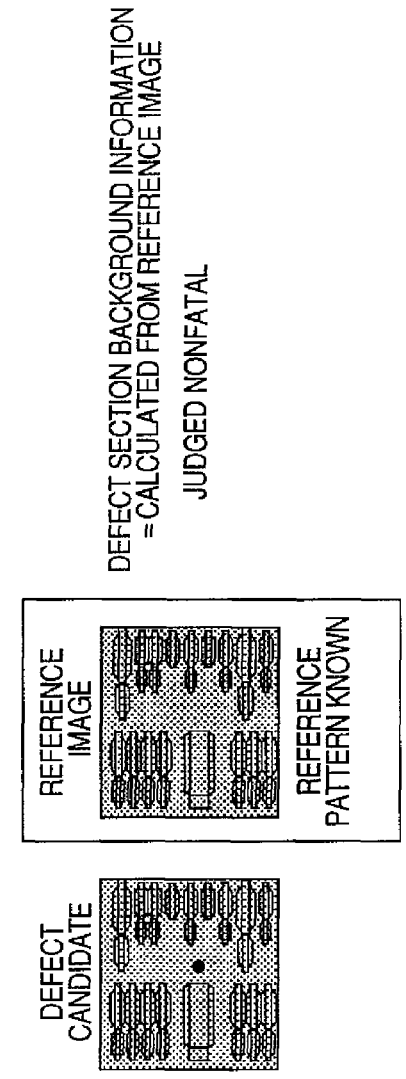
FIG. 17C2

FIG. 20A
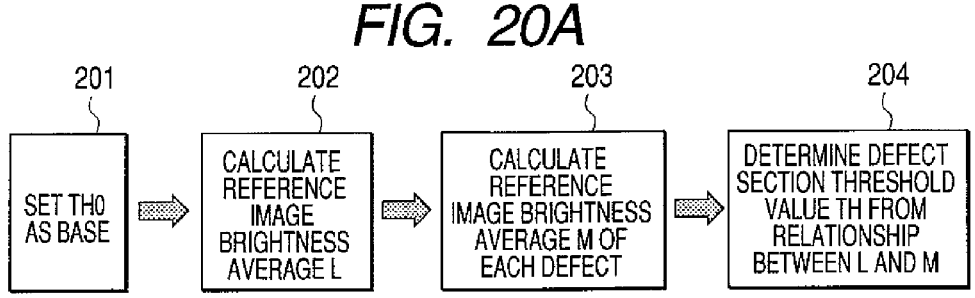
FIG. 20B    FIG. 20C
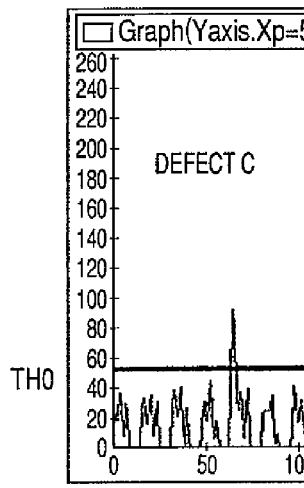
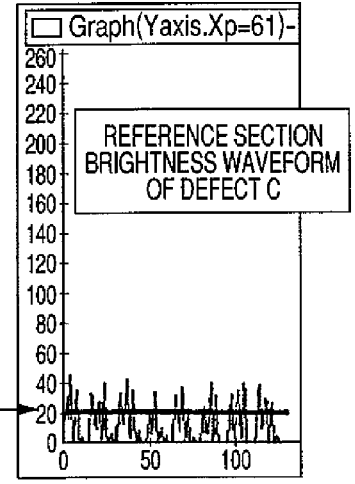
FIG. 20D    FIG. 20E
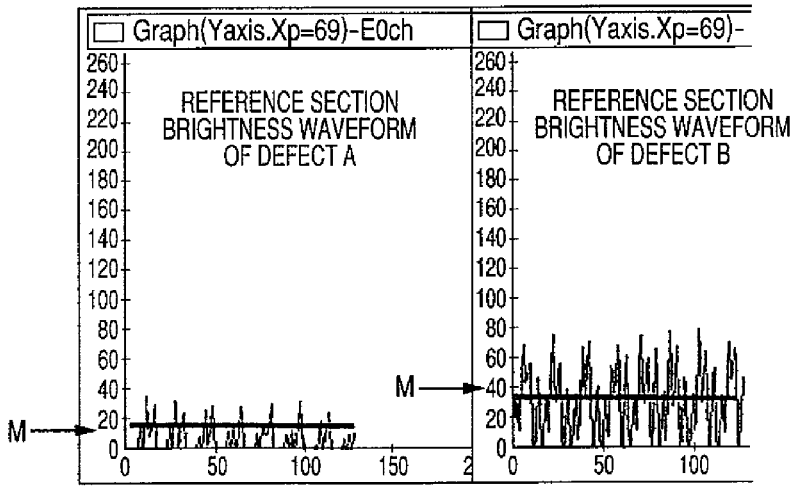

METHOD AND APPARATUS FOR INSPECTING PATTERN DEFECTS

CROSS REFERENCE TO RELATED APPLICATION

This is a continuation of U.S. application Ser. No. 10/992,759, filed Nov. 22, 2004 now U.S. Pat. No. 7,388,979. This application relates to and claims priority from Japanese Patent Application No. 2003-390655, filed on Nov. 20, 2003. The entirety of the contents and subject matter of all of the above is incorporated herein by reference.

BACKGROUND OF THE INVENTION

The present invention relates to an inspection technology for comparing between a detected image and a reference image of an inspection target, which is obtained through the use, for instance, of light or laser beam, and detecting microscopic pattern defects, foreign matter, and the like based on the differences, and more particularly to a pattern defect inspection method and apparatus that are suitable for conducting a visual inspection of semiconductor wafers, TFTs, photomasks, and the like.

A known conventional technology for pattern defect inspection is disclosed, for instance, by Japanese Patent Laid-open No. 2001-5961.

A microscopic defect inspection apparatus is disclosed by Japanese Patent Laid-open No. 2001-5961. This microscopic defect inspection apparatus includes an image signal detection section, an analog-to-digital conversion section, a delay circuit section, a first image processing circuit section, a second image processing circuit section, and a defect judgment section. The image signal detection section, which includes radiation optical system for radiating DUV light having a wavelength of not more than 400 nm, and detection optical system equipped with a TDI image sensor or other similar image sensor, detects image signals having a pixel size of not larger than 0.2 μm from an inspection target and outputs the detected image signals in a parallel manner over a plurality of channels. The analog-to-digital conversion section forms each of the multi-channel image signals that are input in a parallel manner from the image signal detection section. The delay circuit section outputs multi-channel reference image data in a parallel manner. The first image processing circuit section performs a multi-channel, parallel image process to detect a positional displacement between the two types of image data and correct any positional displacement in accordance with the multi-channel detected image data derived from the analog-to-digital conversion section and the multi-channel reference image data derived from the delay circuit section. The second image processing circuit section performs a multi-channel, parallel image comparison process to compare reference image data and detected image data, which is received from the first image processing circuit section and subjected to positional displacement correction on an individual channel basis, and extract information about defect candidate points. The defect judgment section makes a detailed analysis in accordance with the information about multi-channel defect candidate points, which is input from the second image processing circuit section, and judges whether the defect candidate points are true defects.

Circuit patterns formed on semiconductor wafers targeted for inspection have been overly enhanced to a microscopic size of 0.1 μm or smaller while the diameters of semiconductor wafers have been increased. Since the circuit patterns are overly enhanced to a microscopic size, it is demanded that defects, which are smaller than circuit patterns in size, be detected. To fill such a demand, UV light or DUV light is used as the illumination light, and high-magnification detection optical system is used to achieve high resolution and provide a pixel size smaller than the defects to be detected. Consequently, the image information obtained from an inspection target will become huge. Under these circumstances, it is demanded that the obtained image information be rapidly processed to inspect for microscopic defects with high sensitivity and high reliability. However, these requirements are not adequately considered by the aforementioned conventional technology.

Due to the use of a CMP or other polishing method, semiconductor wafers targeted for inspection slightly vary in pattern film thickness. Therefore, local brightness differences are found in the image signals between various chips, which should basically be the same. In FIG. 4A, the reference numeral 41 denotes a typical inspection target image signal. In FIG. 4B, the reference numeral 42 denotes a typical reference image signal. As indicated by 4a in FIGS. 4A and 4b in FIG. 4B, the same patterns of the inspection target image signal and reference image signal differ in brightness. Further, there is an ultramicroscopic defect 4d in 41 in FIG. 4A, which is an inspection target image. In such an instance, the resulting difference image looks like FIG. 4C. The difference image is obtained by generating density differences in accordance with the difference values derived from various locations of the inspection target image and reference image. FIG. 4D shows a waveform that represents difference values derived from locations 1D-1D'. If any difference value exceeding a threshold value TH is labeled as a defect as is the case with the use of a conventional method, the difference value 4c, which represents the difference between patterns 4a and 4b, which differ in brightness, is detected as a defect. This is a problem that a false-information that should not be detected originally as a defect will occur so much. Such a false-information could be avoided, for instance, by increasing the threshold value TH (increasing from TH to TH2 as shown in FIG. 4D). However, the use of such a false-information avoidance method decreases the sensitivity so that the ultramicroscopic defect 4d, which corresponds to a difference value smaller than the increased threshold value, cannot be detected.

SUMMARY OF THE INVENTION

The present invention provides a pattern defect inspection method and apparatus that can reveal ultramicroscopic defects on an inspection target in which ultramicroscopic circuit patterns are formed, and can inspect the defects with high sensitivity and at a high speed.

In other words, the present invention provides a pattern defect inspection apparatus and method for inspecting an inspection target (a sample) for pattern defects. The pattern defect inspection apparatus includes image acquisition means for acquiring a detected image signal and a reference image signal from the inspection target and storing the acquired image signals in an image memory; a defect candidate extraction unit for extracting a defect candidate by comparing a detected image signal with the reference image signal, which are read from the image memory; and a defect detection unit for performing detection process and classification process of defects from (based on) a partial image containing the defect candidate extracted by the defect candidate extraction unit. The process performed by the defect candidate extraction unit and/or the process performed by the defect detection unit is performed asynchronously with the image acquisition process performed by the image acquisition means.

The present invention provides the pattern defect inspection apparatus and method. The process performed by the defect detection unit, the process performed by the defect candidate extraction unit, and the image acquisition process performed by the image acquisition means, are performed asynchronously with each other. The defect candidate extraction unit includes a memory that stores a partial image containing an extracted defect candidate and the feature amount of defect candidate.

The image acquisition means according to the present invention includes a plurality of image sensors for performing an image acquisition process on a plurality of areas on the inspection target in a parallel manner.

The defect candidate extraction unit according to the present invention performs a defect candidate extraction process for a plurality of areas on the inspection target in a parallel manner.

The defect detection unit according to the present invention performs a detection process and a classification process of defects in a parallel manner based on a plurality of partial images containing a defect candidate.

The defect candidate extraction unit according to the present invention includes a positional displacement detection section for calculating the amount of positional displacement between the detected image signal and reference image signal for each field unit, a brightness correction section for calculating the amount of signal correction for adjusting the brightness difference between the detected image signal and reference image signal, for each area and an image comparison section for performing a brightness comparison at corresponded positions between the detected image signal and reference image signal by using the positional displacement amount, which is calculated for the each field unit by the positional displacement detection section, and the signal correction amount, which is calculated for the each area by the brightness correction section.

The present invention is such that the parallel processing counts for the defect candidate extraction unit and defect detection unit are set as appropriate in accordance with the amount of image data acquired by the image acquisition means.

The threshold value (inspection sensitivity) for the detection process and the classification process of the defects performed by the defect detection unit according to the present invention is automatically set in accordance with feature amounts such as the brightness, contrast, and pattern density of a partial image containing defect candidate.

The defect detection unit according to the present invention includes a comparative collation section, which detects defects only by collating the feature amount of defect candidate, which is calculated by the defect candidate extraction unit at the time of defect candidate extraction, with the feature amount of defect candidate, which is calculated by the defect detection unit at the time of defect detection.

The threshold value for classifying defect candidates into a plurality of types in the defect detection unit according to the present invention is set for each of the partial images becoming a target (an object) for classification.

The threshold value for classifying defect candidates into a plurality of types in the defect detection unit according to the present invention is calculated from a plurality of partial images.

The defect detection unit according to the present invention includes an output monitor section, which displays the results of the detection process and the classification process of the defect.

The defect detection unit according to the present invention examines the defect candidate extraction results by performing multi-step positional displacement detection processes, which vary in processing range (processing unit) or processing method, and multi-step brightness correction processes, which vary in processing range (processing unit) or processing method.

The present invention makes it possible to reveal ultramicroscopic defects on an inspection target in which ultramicroscopic circuit patterns are formed, and inspect the defects with high sensitivity and at a high speed.

Further, the present invention makes it possible to attain an inspection speed that corresponds to the processing speed, which is determined, for instance, by the image sensor's image acquisition rate, image accumulation time, and scanning width.

These and other objects, features and advantages of the present invention will be apparent from the following more particular description of preferred embodiments of the invention as illustrated in the accompanying drawings.

BRIEF DESCRIPTION OF THE DRAWINGS

FIG. 12 is a flowchart illustrating a process that a brightness correction section according to one embodiment of the present invention performs to adjust brightness differences, which randomly arise.

FIG. 14 illustrates how the brightness correction amount is calculated by a brightness re-correction section according to one embodiment of the present invention.

FIG. 15A shows a reference image. FIG. 15B shows area B of the reference image and its scatter diagram. FIG. 15C shows area C of the reference image and its scatter diagram.

FIGS. 16A1 and 16A2 show the images of a defect candidate at one same location. FIG. 16A3 shows an image that indicates a detection result. FIGS. 16B1 and 16B2 show the images of a defect candidate at one same location. FIG. 16B3 shows an image that indicates a detection result.

FIG. 17C1 shows the images of chips 1 and 2, which are compared by a defect candidate extraction unit 15. FIG. 17C2 shows a defect candidate image and its reference image, which are compared by a defect detection unit 16.

FIG. 20A is a flowchart illustrating an automatic defect classification process according to one embodiment of the present invention. FIG. 20B is a brightness waveform diagram that is obtained in a case where threshold value TH0 is set in accordance with typical or standard defect C. FIG. 20C is a brightness waveform diagram that is obtained in a case where reference brightness value L is calculated from a reference image (background image) of typical or standard defect C for which threshold value TH0 is set. FIGS. 20D and 20E are brightness waveform diagrams that are obtained in cases where brightness value M is calculated from reference sections of defects A and B, which are shown in FIGS. 19A and 19B.

DETAILED DESCRIPTION OF THE PREFERRED EMBODIMENTS

Embodiments of the present invention will now be described in detail with reference to FIGS. 1 through 20.

Figure 1:
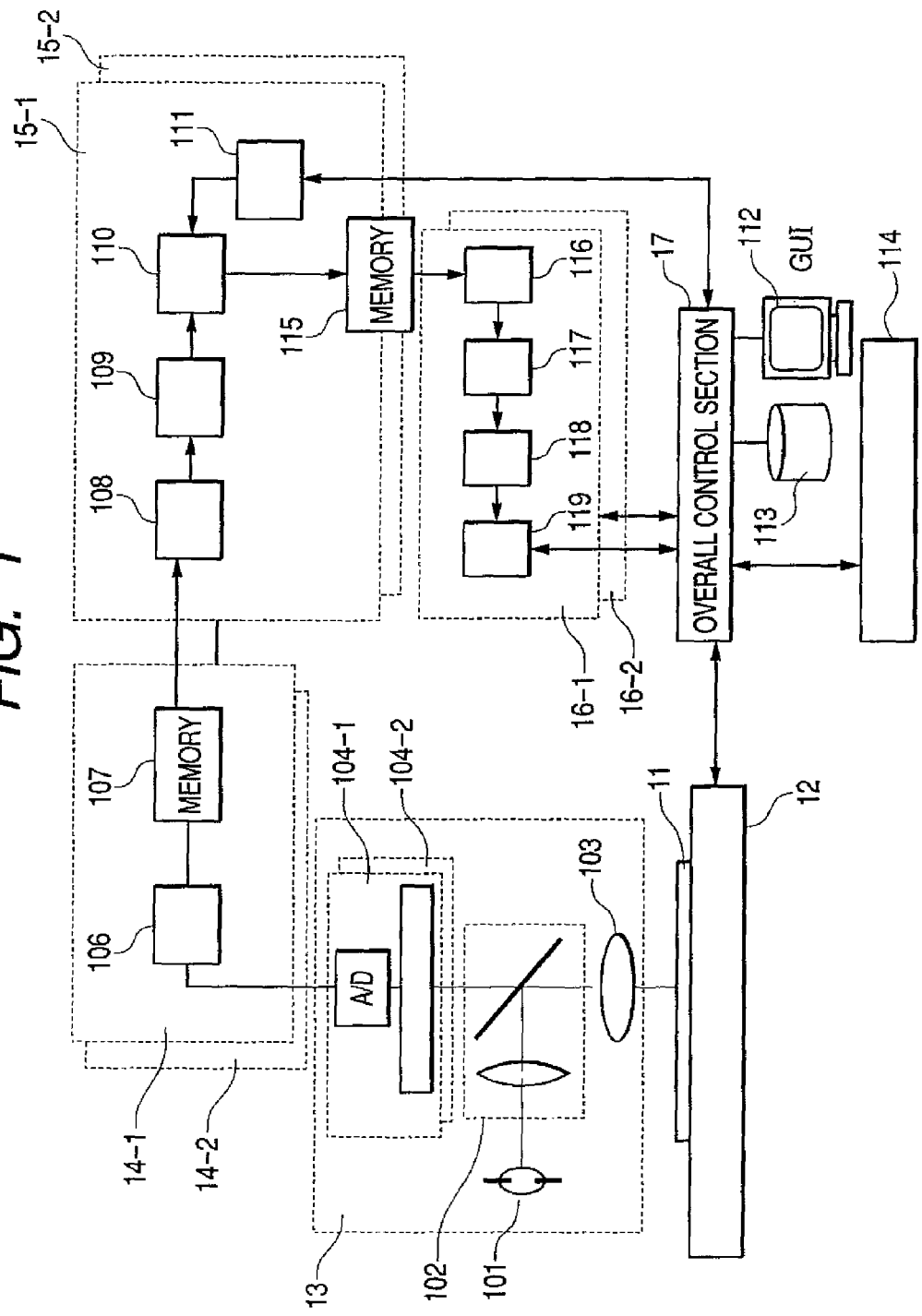
FIG. 1 illustrates the configuration of one embodiment of a pattern defect inspection apparatus according to the present invention.

FIG. 1 illustrates the configuration of an optical visual inspection apparatus that inspects semiconductor wafers in accordance with one embodiment of the present invention. The optical visual inspection apparatus includes a stage 12 and a detection unit (image acquisition means) 13. The stage 12 moves while a sample (e.g., a semiconductor wafer or other inspection target on which a 0.1 μm or smaller ultramicroscopic circuit pattern is formed) 11 is mounted on it. The detection unit 13 includes an illumination optical system 102 for condensing the light emitted from a light source 101 and illuminating the condensed light on the sample 11, an image formation lens (objective lens included) for forming an optical image that is reflected from the sample 11, and an image detection section 104, which includes an image sensor for receiving the formed optical image and converting it into an image signal in accordance with its brightness and an analog-to-digital conversion section for converting the input signal from the image sensor to a digital signal (a gradation signal). The image detection section 104 includes one or more sets (104-1, 104-2).

In the example shown in FIG. 1, a lamp is used as the light source 101. Alternatively, however, a laser may be used as the light source 101. The light emitted from the light source 101 may have a narrowband short wavelength. Alternatively, wideband wavelength light (white light) may be used. If short wavelength light is used, ultraviolet light (UV light) may be used to raise the resolution of the image to be detected (to detect microscopic defects).

A time delay integration image sensor (TDI image sensor) may be used as the image sensor 104. The TDI image sensor is formed by arranging a plurality of one-dimensional image sensors in a two-dimensional manner. When each one-dimensional image sensor detects a signal in synchronism with the movement of the stage 12 and transfers the detected signal to the next one-dimensional image sensor for addition purposes, high-sensitivity detection can be achieved at a relatively high speed. It goes without saying that a CCD linear sensor may alternatively be used as the image sensor 104.

The reference numeral 14 denotes an image editing section, which includes a preprocessing section 106 and an image memory 107. The preprocessing section 106 performs an image correction process on the digital signal (the gradation signal) of the image detected by the detection unit (image acquisition means) 13 to provide, for instance, shading and dark level corrections. The image memory 107 stores the digital signal of a detected image targeted for comparison and the digital signal of a reference image. The image editing section 14 includes one or more sets (14-1, 14-2).

The write into the image memory 107 and the read from the image memory 107 are performed at different times.

The reference numerals 15 and 16 denote a defect candidate extraction unit and a defect detection unit, respectively. These units perform a defect candidate extraction process on an acquired image and a detection process/a classification process of defects on a partial image containing defect candidates asynchronously with a detection process (image acquisition process) on an image from the image sensor that is performed by the detection unit 13 and image editing section 14. The defect candidate extraction unit 15 and defect detection unit 16 will now be described.

The defect candidate extraction unit 15 extracts a partial image containing defect candidates within a wafer, which serves as the sample 11, asynchronously with a detection process performed on an image from the image sensor. The defect candidate extraction unit 15 includes (comprises) one or more sets (15-1 and 15-2 within the configuration shown in FIG. 1). The defect candidate extraction unit 15 compares two digital image signals (the digital signal of a detected image and the digital signal of a reference image) that are stored in the image memory 107 of the image editing section 14. If any difference value is greater than a threshold value, the corresponded portion is extracted as a defect candidate. First, the digital signal of a detected image and the digital signal of a reference image, which are stored in the image memory 107, are read. Then, a positional displacement detection section 108 calculates the amount of positional displacement for positional displacement adjustment purposes, and a brightness correction section 109 calculates the amount of signal correction for the purpose of adjusting the difference between the brightness of the detected image (brightness value) and the brightness of the reference image (brightness value). An image comparison section 110 compares the corrected brightnesses at the corresponded positions of the detected image and reference image digital signals (corresponded positions aligned by pixel unit in both images) by using the calculated positional displacement amount and signal correction amount. If any difference value of the corrected brightness is greater than a predetermined threshold value, the corresponded portion is extracted as a defect candidate, and the amounts of feature (brightness value, dimensions, area, coordinates, difference from reference image, etc.) of the defect candidate are calculated.

In other words, the image comparison section 110 compares the image signals of the detected image and reference image based on combining the decomposition of the scatter diagram and spatial information of feature so as to mention later, by using, for instance, the calculated positional displacement amount. If any difference value between both the image signals is greater than a predetermined threshold value, the image comparison section 110 extracts the corresponded portion as a defect candidate and calculates the amounts of feature of the defect candidate. The image comparison section 110 then stores a partial image containing the defect candidate, its reference image, the amounts of feature of the defect candidate, and inter-image positional displacement amount in the memory 115. A threshold value setup section 111 sets a threshold value, which is used to extract defect candidates from difference values, for each area within a chip, and then gives the threshold value to the image comparison section 110. The defect candidate extraction units 15-1, 15-2 perform parallel processing by performing the same procedure.

The write into the memory 115 and the read from the image memory 115 are performed at different times.

The defect detection unit 16 detects defects from defect candidates extracted by the defect candidate extraction units 15 and classifies the detected defects according to the amounts of feature. The defect detection unit 16 also performs the above detection/classification process asynchronously with a detection process that is performed on an image fed from the image sensor. Therefore, the defect detection unit 16 includes (comprises) one or more sets (16-1 and 16-2 within the configuration shown in FIG. 1), as is the case with the defect candidate extraction unit 15. The defect detection unit 16 reads the digital signal of a partial image containing defect candidates and the digital signal of its reference image, which are stored in the image memory 115. A positional displacement re-detection section 116 recalculates the amount of positional displacement. A brightness re-correction section 117 calculates the amount of signal correction for adjusting the difference between the brightness of the detected image (brightness value) and the brightness of the reference image (brightness value). An image re-comparison section 118 compares the corrected brightnesses at the corresponded positions of the detected image and reference image digital signals (corresponded positions aligned by pixel unit in both images) by using the calculated positional displacement amount and signal correction amount. If any difference value of the corrected brightness is greater than a predetermined threshold value, the image re-comparison section 118 extracts the corresponded portion as a defect, and calculates the amounts of its feature. A defect classification section 119 collates the amounts of the feature of the defect candidate, such as a brightness value, dimensions, area, coordinates, and difference with reference image, and the amount of positional displacement between both images calculated by the defect candidate extraction unit 16, with the similar amounts of feature of the defect portion and of positional displacement between both images that are calculated by the defect detection unit 15, and judges whether a defect candidate is a true defect or a false-information. True defects will be classified into a plurality of categories. The defect classification section 119 automatically sets a classification threshold value as needed for each defect image. The defect detection units 16-1, 16-2 perform parallel processing by performing the same procedure.

An overall control section 17 includes (comprises) a user interface section 112, which includes display means and input means for receiving a user's request for changes in inspection parameters (e.g., a threshold value for image comparison) and displaying detected defect information; a storage device 113 for storing, for instance, the amounts of feature and images of the detected defect candidate; and a CPU (incorporated in the overall control section 17) for exercising various control functions. A mechanical controller 114 complies with a control command from the overall control section 17, to drive and control, for example, the stage and optical components incorporated in detection unit 13. The defect candidate extraction units 15-1, 15-2 and defect detection units 16-1, 16-2 are also driven in accordance with a command from the overall control section 17.

Figure 6:
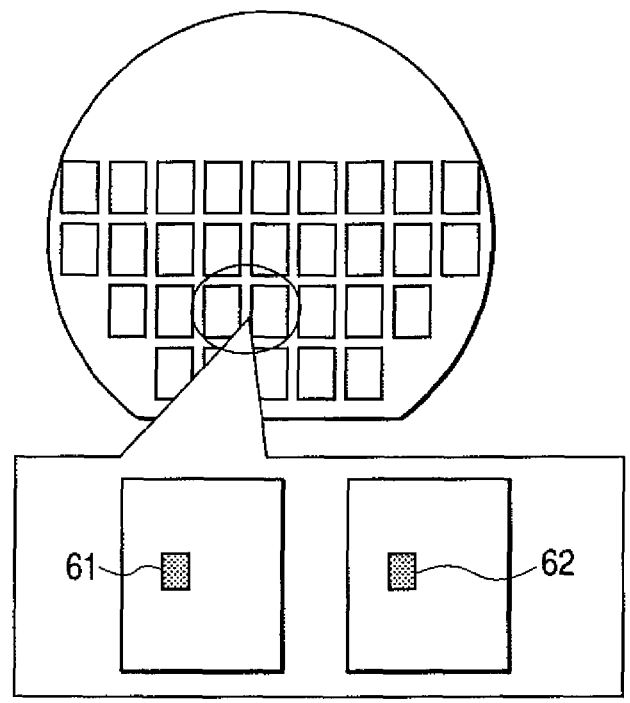
FIG. 6 shows an example of an image comparison process unit.

As shown in FIG. 6, a large number of chips having the same pattern are regularly arranged on a semiconductor wafer 11 that is to be inspected. In the inspection apparatus shown in FIG. 1, the overall control section 17 uses the stage 12 to continuously move the semiconductor wafer 11, which is a specimen. In synchronism with such movement, the detection unit 13 sequentially acquires a chip image. The same positions of two adjacent chips are compared two times. More specifically, the digital image signals, for instance, of areas 61 and 62 in FIG. 6 are extracted as a detected image and a reference image, respectively, and compared two times in the above-mentioned sequence. Any difference encountered as a result of comparison is detected as a defect and then classified.

Figure 8:
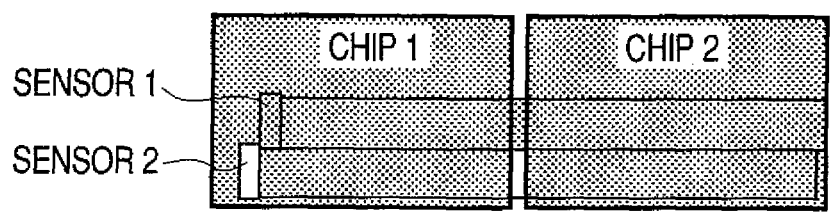
FIG. 8 illustrates a first embodiment according to the present invention in which images are acquired by two image detection units (image acquisition means) in a parallel manner.
Figure 9:
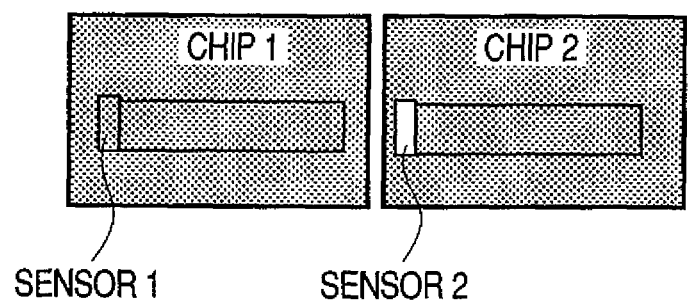
FIG. 9 illustrates a second embodiment according to the present invention in which images are acquired by two image detection units (image acquisition means) in a parallel manner.
Figure 10:
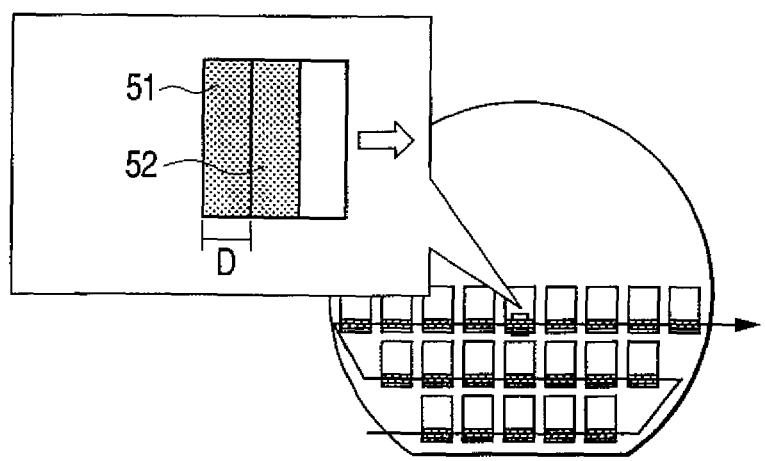
FIG. 10 illustrates individual fields for which the amount of positional displacement between two images according to the present invention is calculated to achieve alignment by pixel unit.

When the inspection apparatus according to the present invention is configured to incorporate two image detection sections 104-1, 104-2 and perform an image pickup process in a parallel manner, it is possible, as shown in FIGS. 8 and 9, to pick up images at different positions, which are formed by an image formation lens 103. FIG. 8 shows a case where two image sensors 104-1, 104-2 are arranged in a direction crossing (e.g., perpendicular to) the advance direction (the scanning direction) of stage to achieve image acquisition and analog-to-digital conversion in a parallel manner for the purpose of picking up the image of an inspection target chip 1 and the image of a reference chip 2, which is to be compared with the inspection target chip 1. FIG. 9 shows a case where two image sensors 104-1, 104-2 are arranged in the advance direction of stage with a spacing interval equivalent to one chip provided between the image sensors to achieve image acquisition in a parallel manner, that is, acquire the image of chip 1 with image sensor 1 and the image of chip 2 with image sensor 2 and achieve analog-to-digital conversion.

As described above, when a plurality of image detection sections 104 are provided to perform a parallel operation, image acquisition can be accomplished at a high speed without regard to the image sensor processing speed. The images acquired by the image sensors 104-1, 104-2 are processed respectively by the image editing sections 14-1, 14-2 and stored respectively in the image memories 107-1, 107-2. It goes without saying that the image detection section 104 and image editing section 14 may each include as one set.

Figure 2:
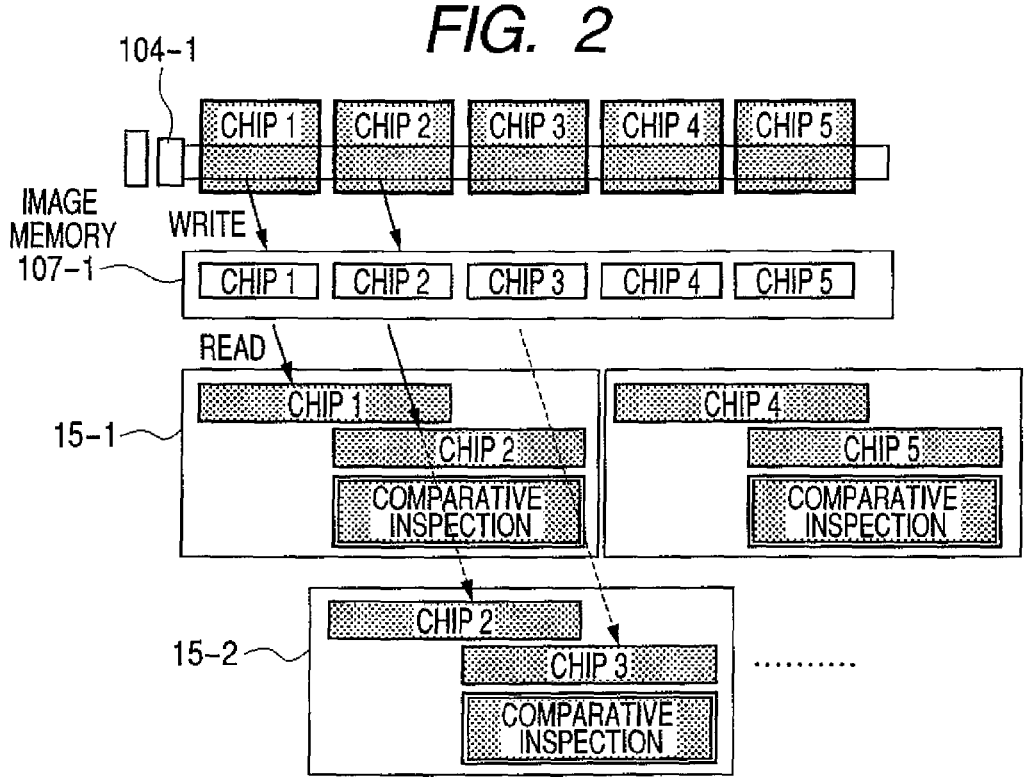
FIG. 2 illustrates a parallel process that a defect candidate extraction unit according to one embodiment of the present invention performs to compare two images.

The defect candidate extraction unit 15 and defect detection unit 16 according to the present invention perform the process for extracting defect candidates from an acquired image and the process for detecting defects from a partial image containing defect candidates and classifying the detected defects. These processes are performed asynchronously with the process for detecting images from the image sensors and will now be described with references to FIGS. 2 and 3. It goes without saying that the process of the defect candidate extraction unit 15 may be performed asynchronously with the process of the defect detection unit 16. FIG. 2 illustrates a first embodiment and indicates how an image acquired by one image detection section (image sensor) 104-1 is processed. In the embodiment to be described, images sequentially acquired by the image detection section 104-1 and stored in the image memory 107-1 are processed in a parallel manner by two defect candidate extraction units 15-1, 15-2. These stored images indicate the corresponded locations of chips 1, 2, 3, and so on. Defect candidate extraction unit 15-1 reads the images of chips 1 and 2 from the memory 107-1 and performs the above-mentioned series of processing steps to extract defect candidates. In parallel with such defect candidate extraction, defect candidate extraction unit 15-2 reads the images of chips 2 and 3 from the memory 107-1 and performs a series of processing steps to extract defect candidates. Defect candidates whose coordinates in units 15-1 and 15-2 agree with each other are extracted as defect candidates of chip 2. A partial image of chip 2, which contains detected defect candidates, and either or both of the corresponded partial images of chips 1 and 3 are stored in memory 115 as reference images. In this instance, memory 115 also stores, for example, the amount of positional displacement between images for comparison and the amount of feature of defect candidate. Subsequently, defect candidate extraction unit 15-1 reads the images of chips 4 and 5 from memory 107-1 and performs the above-mentioned series of processing steps to achieve defect candidate extraction. In parallel with such defect candidate extraction, defect candidate extraction unit 15-2 reads the images of chips 5 and 6 from memory 107-1 and performs a series of processing steps to achieve defect candidate extraction. Defect candidates whose coordinates in units 15-1 and 15-2 agree with each other are extracted as defect candidates of chip 5. A partial image of chip 5, which contains detected defect candidates, and either or both of the corresponded partial images of chips 4 and 6 are stored in memory 115 as reference images.

As described above, even when the processing speed of the defect candidate extraction unit is half the sensor's image acquisition processing speed, defect candidate extraction can be achieved in synchronism with the sensor's image acquisition. Further, the image pickup process and defect candidate extraction process may be performed asynchronously with each other when image memory 107 is used as an intervening device.

Figure 3:
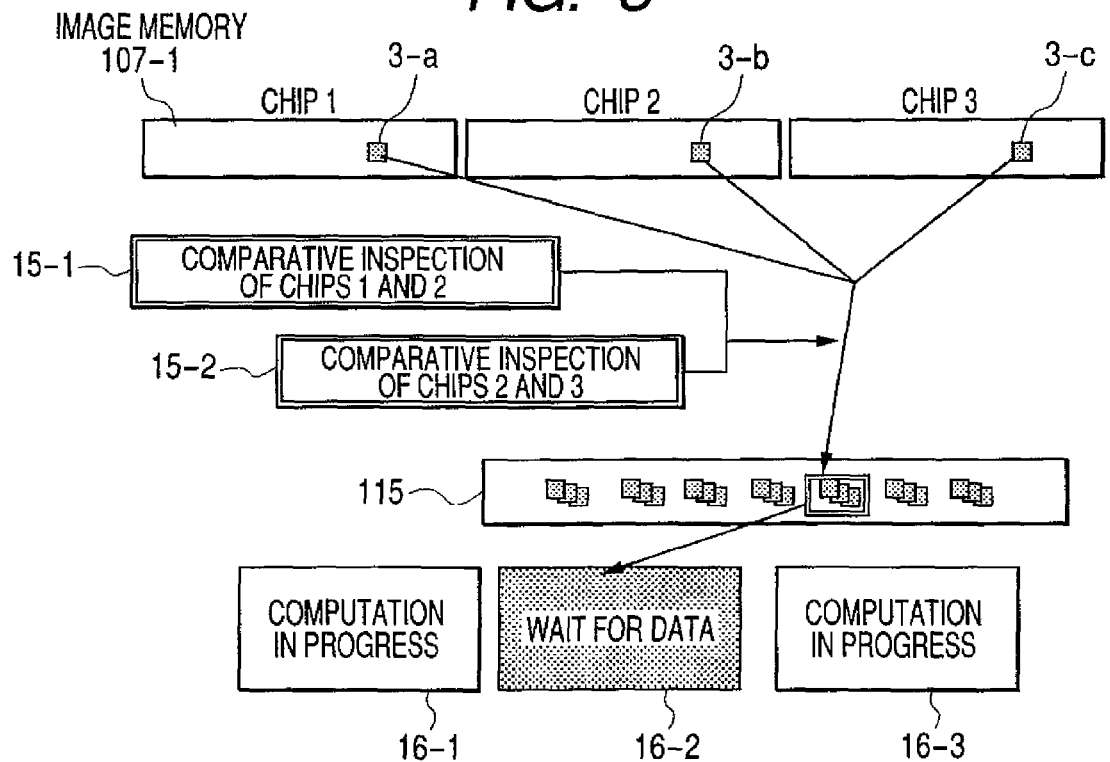
FIG. 3 illustrates a parallel process that a defect candidate extraction unit according to another embodiment of the present invention performs to compare two images.
Figure 4A:
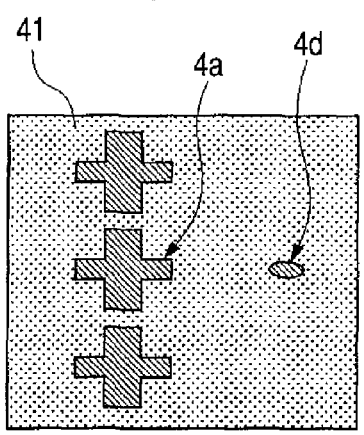
FIG. 4A shows an inspection target image signal.
Figure 4B:
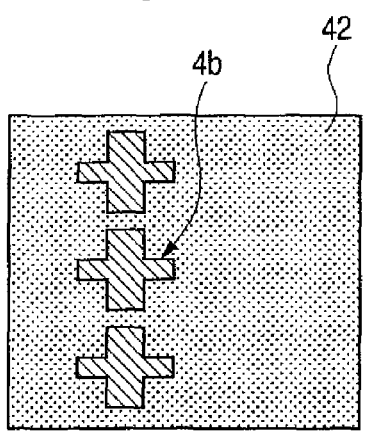
FIG. 4B shows a reference image signal.
Figure 4C:
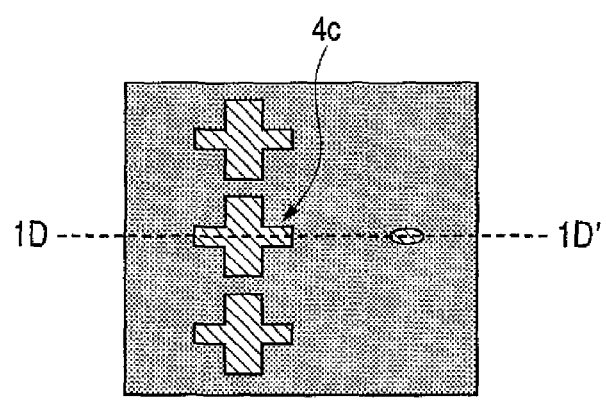
FIG. 4C shows a difference image that indicates the difference between the inspection target image signal shown in FIG. 4A and the reference image signal shown in FIG. 4B.
Figure 4D:
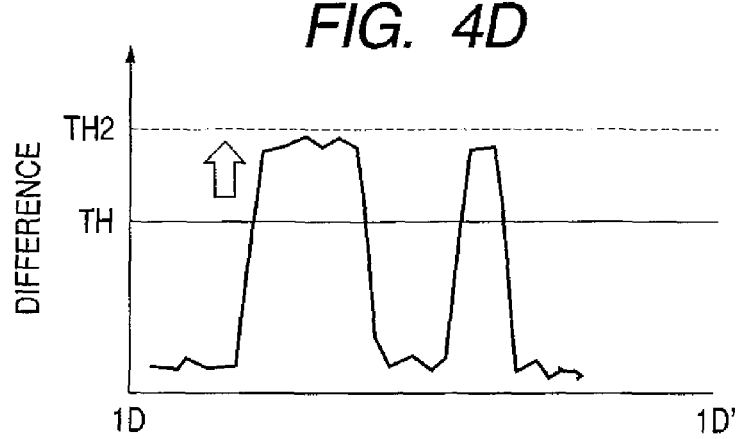
FIG. 4D shows a difference image signal waveform that prevails at locations 1D-1D' in FIG. 4C.

FIG. 3 illustrates a second embodiment and indicates image processing steps that are performed to detect defects from a partial image containing extracted defect candidates and classify the detected defects. The reference numeral 3-*b* in FIG. 3 denotes a partial image containing defect candidates that are extracted because their coordinates in units 15-1 and 15-2 agree with each other. The reference numerals 3-*a* and 3-*c* denote partial images that correspond to partial image 3-*b*. After partial image 3-*b*, either or both of partial images 3-*a* and 3-*c*, the amount of feature, and the amount of positional displacement are stored in memory 115, the defect detection unit 16 reads two partial images (3-*b* and 3-*a* or 3-*b* and 3-*c*) or three partial images (3-*b*, 3-*a*, and 3-*c*), the amount of feature, and the amount of positional displacement from memory 115 and performs a series of processing steps. The inspection apparatus according to the present invention includes three defect detection units 16-1, 16-2, 16-3. These defect detection units are configured so as to perform parallel processing. As regards a partial image that contains defect candidates and is to be temporarily stored in memory 115, the overall control section 17 monitors the operations of the three defect detection units, and exercises control so that processing is performed by a defect detection unit that is not engaged in arithmetic processing (is waiting for data). This ensures that the defect detection process and defect classification process are performed efficiently at a high speed. In the present embodiment, memory 115, which stores a partial image containing defect candidates, the corresponded reference image, and the amount of feature, is common in the two defect candidate extraction units 15-1, 15-2. Alternatively, however, each of the two defect candidate extraction units may possess such a memory or may not possess such a memory. When memory 115 is used as an intervening device, the defect candidate extraction process can be performed asynchronously with the defect detection process and defect classification process. However, if no such memory is available, the defect detection and defect classification processes are performed in real time and in synchronism with the defect candidate extraction process.

Figure 5:
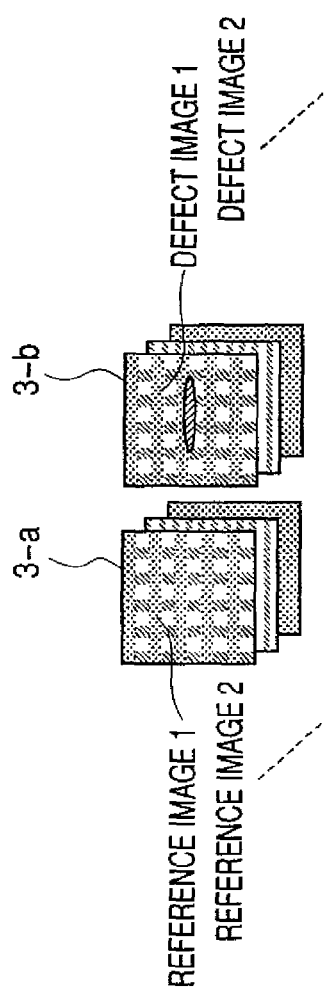
FIG. 5 illustrates information that is stored in a memory and transferred to a defect detection unit in accordance with one embodiment of the present invention.

FIG. 5 shows one embodiment of information that is stored in memory 115 and transferred to the defect detection unit 16. Partial image sets 3-*a* (reference images 1, 2, and so on) and 3-*b* (defect images 1, 2, and so on), which both contain defect candidates, are serially numbered (assigned defect candidate numbers). Memory 115 stores the feature amounts (defect candidate detection position (X,Y) in chip, brightness value, area, and X- and Y-direction dimensions) corresponded with the serial numbers, and X- and Y-direction positional displacement amounts of both images, with partial images (3-*a* and 3-*b*) containing defect candidates.

Even if the image acquisition process differs in processing speed from the process for extracting defect candidates from an acquired image, that is, the processing speed of the defect candidate extraction unit 15 is lower than the speed of target chip image acquisition by the image sensor 104 and the speed of image editing, the inspection speed can be synchronized with the acquisition speed of the image sensor 104 by allowing a plurality of defect candidate extraction units 15 to perform parallel processing. Further, when a partial image containing defect candidates extracted by the defect candidate extraction unit 15 is reprocessed in a parallel manner by a plurality of defect detection units 16, the defect detection process and defect classification process can be performed in real time even if the processing speed of the defect detection unit 16 is lower than that of the defect candidate extraction unit 15. As a result, the inspection/classification speed can be synchronized with the acquisition speed of the image sensor 104. If, for instance, the result of calculations performed, for instance, on the amount of acquired light indicates that the maximum image acquisition speed of the image sensor 104 is 3.2 Gpps (pps: pixels per second), an inspection processing speed of 3.2 Gpps can be attained by using the configuration described above even in a situation where the processing speed of the defect candidate extraction unit 15 is half the maximum image acquisition speed of the image sensor 104, that is, 1.6 Gpps. Further, even if the processing speed of the defect detection unit 16 is half the processing speed of the defect candidate extraction unit 15, that is 0.8 Gpps, the use of the configuration described above makes it possible to attain an inspection processing speed of 3.2 Gpps. Even when the speed of the image sensor 104 is higher than indicated above, the same result can be obtained by allowing an increased number of defect candidate extraction units 15 and defect detection units 16 to perform parallel processing on the acquired image signal. Further, the same result can also be obtained even if the image acquisition width of the image sensor 104 is increased. Furthermore, even if the inspection image magnification is increased (the magnification of the image formation lens 103 is increased) to provide higher inspection sensitivity, the same inspection speed as for the previously employed magnification can be maintained by allowing the employed configuration to include an increased number of defect candidate extraction units 15 and defect detection units 16.

The embodiment described above assumes that the image sensor 104 generates a single output. However, even if the image sensor 104 has a plurality of output terminals and outputs a plurality of signals in a parallel manner, signal processing can be performed in the same manner as described in conjunction with the embodiment described above to perform image processing at a higher speed. In such an instance, the image sensor 104 has a plurality of signal lines, which are connected respectively to a plurality of analog-to-digital converters 105. The outputs generated by these analog-to-digital converters 105 enter the image editing section 14 in which processing is performed in a sequence described above.

Figure 11:
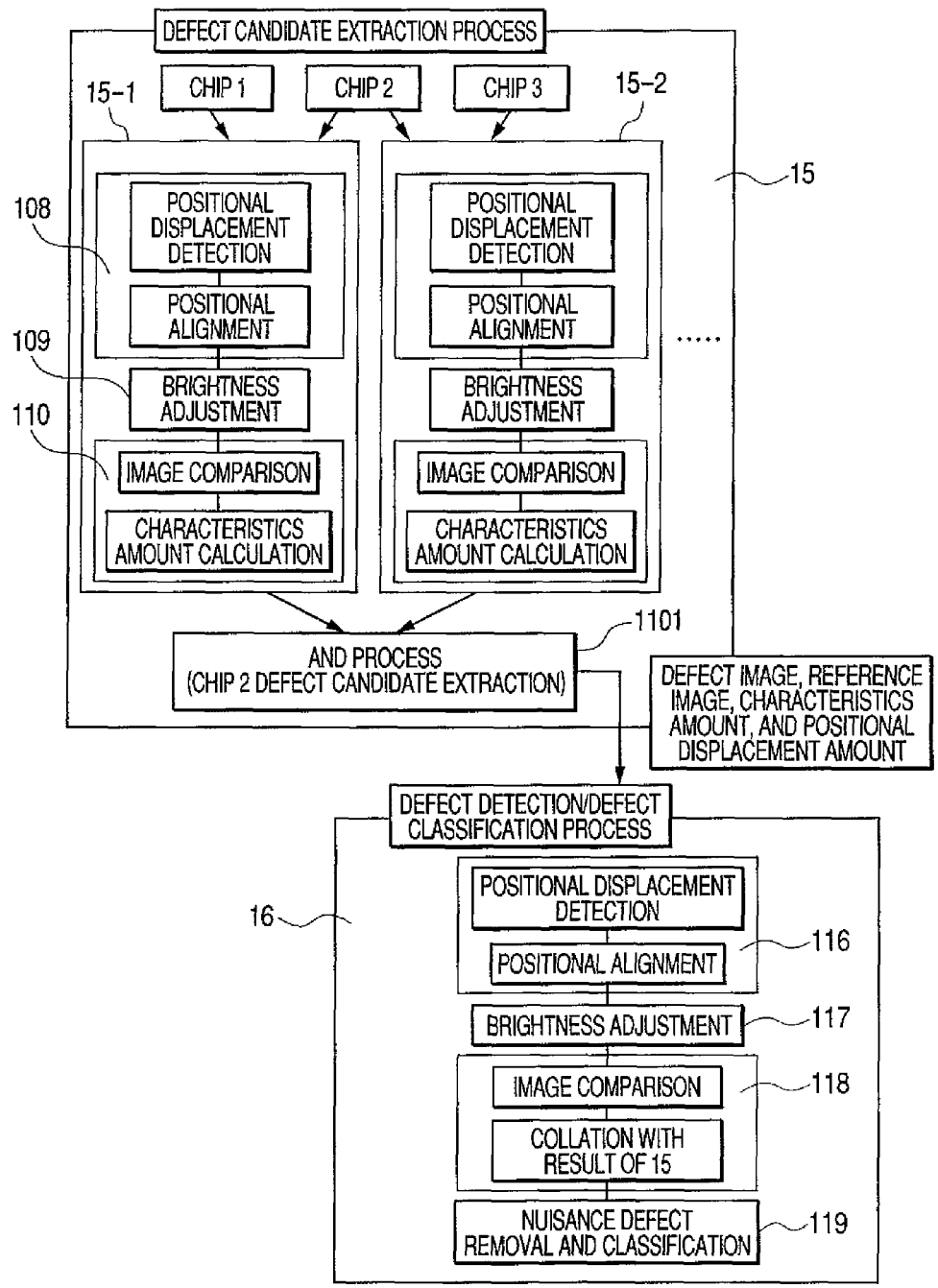
FIG. 11 illustrates processes that a defect candidate extraction unit and defect detection unit perform in accordance with one embodiment of the present invention.

The processes performed by the defect candidate extraction unit 15 and defect detection unit 16 will now be described with reference to FIG. 11. First of all, the detected image signal (the image signal of chip 2 in the example shown in the figure) and the reference image signal (the image signal of chip 1 in the example shown in the figure), which are successively input into memory 107 in synchronism with the movement of the stage 12, are read. The image signals of these two chips do not represent the same location at all if the stage 12 vibrates or the wafer mounted on the stage is tilted. Therefore, the positional displacement detection section 108 calculates the amount of positional displacement between the two images (hereinafter referred to as the positional displacement amount). The calculation of the positional displacement amount performs specific length in the advance direction of a stage one by one as one processing unit. The reference numerals 51 and 52 in FIG. 10 respectively denote a processing area for a situation where length D (pixel) is one processing unit. This unit processing area is hereinafter referred to as a field.

As described above, the positional displacement detection section 108 calculates the amount of positional displacement between field 51 and its corresponding adjacent chip field, and then calculates the amount of positional displacement between field 52 and its corresponding adjacent chip field. In other words, the positional displacement detection section 108 sequentially calculates the positional displacement amount for each field unit in response to an entered image. The positional displacement amount may be calculated by various methods. For example, the positional displacement amount may be calculated by inter-image normalized cross-correlation, inter-image density difference summation, or inter-image density difference sum-of-squares calculation. Any of these methods will do. In accordance with the calculated positional displacement amount, the positions of two images are then aligned for each field unit.

If the aforementioned image sensor 104 is connected to a plurality of analog-to-digital converters 105 via a plurality of signal lines and the outputs generated by the A/D converters enter the image processing section 14, positional displacement amount calculation for each field unit and positional alignment are both performed in a parallel manner. The unit of parallel processing, which is performed with divisions provided in a direction nearly perpendicular to the advance direction of stage, is hereinafter referred to as a channel. To achieve high-precision positional alignment on an individual channel basis, it is possible to extract only high-reliability positional displacement amounts (e.g., those having a high correlation coefficient) from those calculated on an individual channel basis, add up a plurality of sets of extracted positional displacement information, and calculate the positional displacement amount of a low-reliability channel. In one embodiment, all the channels are examined so that the positional displacement amount of the highest-reliability channel is regarded as the positional displacement amount of a low-reliability channel. Further, a plurality of sets of high-reliability positional displacement information are added up to calculate a positional displacement amount that is common to all channels and use the calculation result as the positional displacement amount of each channel. It is also possible to calculate the positional displacement amount of a low-reliability channel by performing an interpolation or extrapolation process on the positional displacement amounts of a plurality of high-reliability channels. The interpolation or extrapolation process may be performed by means of linear interpolation or by means of spline approximation or other curve approximation. This ensures that even when a limited amount of pattern information is available from a channel for positional displacement amount calculation, it is possible to effect positional alignment in accordance with an image distortion arising, for instance, out of stage vibration.

Next, the brightness correction section 109 calculates a signal correction amount for adjusting a brightness difference between two positionally aligned images. Brightness differences may arise due, for instance, to (1) a slight film thickness difference of semiconductor wafer chips to be inspected, (2) sensitivity differences among image sensor pixels, (3) light amount differences accumulated in the image sensor by stage speed irregularities, and (4) changes in the amount of illumination light. Difference (1) arises randomly depending on the semiconductor wafer pattern. Differences/changes (2), (3), and (4) are specific to the employed inspection apparatus and generate in line form or stripe form on the detected image signal. The present invention adjusts any brightness difference that arises due to (1), (2), (3), or (4). The brightness difference adjustment sequence according to one embodiment is shown in FIG. 12.

Figure 13A:
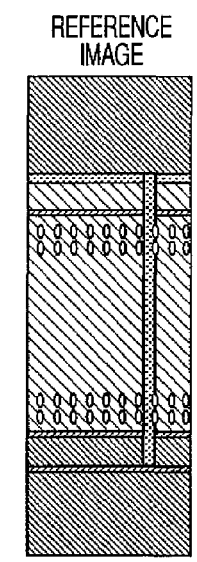
FIG. 13A shows a detected image.
Figure 13B:
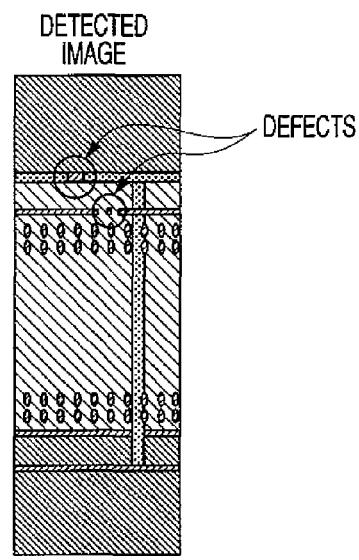
FIG. 13B shows a reference image.
Figure 13C:
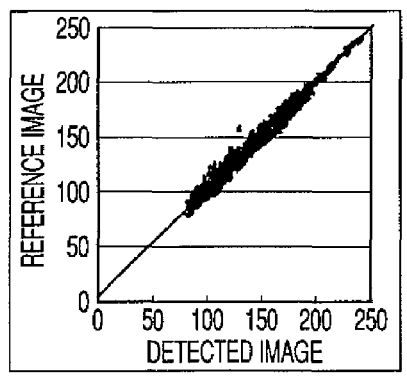
FIGS. 13C through 13E are scatter diagrams in which the brightness of a detected image is plotted along the X-axis and the brightness of a reference image is plotted along the Y-axis.
Figure 13D:
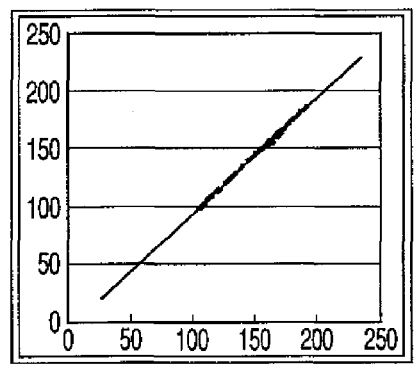
Figure 13E:
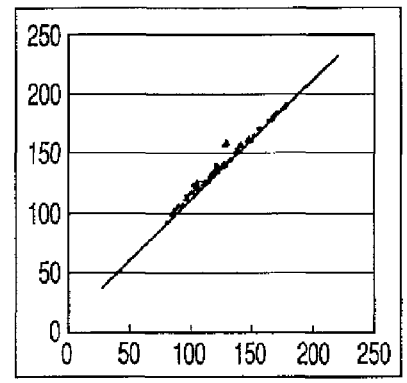

First, step 12-1 is performed to calculate the feature amounts of each corresponding pixel for each specific field and form a two- or more-dimensional feature (characteristics) space. This step is performed for both the detected image and reference image. Any feature amounts will do as far as they indicate the pixel feature, including segments of pixel contrast, brightness, secondary differential value, gradation (gray scale) difference between corresponded pixels, and dispersion value (variation value) used neighboring pixel. Next, step 12-2 is performed to divide the feature space into a plurality of segments. Step 12-3 is then performed to calculate the correction amount for each segment by using the statistics of pixels belonging to each segment. This is the same as for preparing a scatter diagram in which the X-axis and Y-axis indicate the detected image brightness and reference image brightness, respectively, to depict the pixels within the detected image (FIG. 13A) and reference image (FIG. 13B) areas as indicated in FIG. 13C, dividing the scatter diagram into FIGS. 13D, 13E, and so on in accordance with the feature amounts, and calculating the correction amounts within each resulting scatter diagram. As regards the correction amounts for the scatter diagrams, which are obtained by dividing the feature space into segments, a linear expression is determined, as indicated in FIGS. 13D and 13E, by least squares approximation within a scatter diagram. The gradient and y-intercept are used as the correction amounts. The field for forming the feature spaces can be arbitrarily set as far as it is 1×1 pixel or larger. However, if a 1×1 pixel field, which represents the highest frequency, is used for correction purposes, defects will also be united (be corrected) together. Therefore, the field for forming the feature spaces needs to set as a little large area from the 1×1 pixel field. The method for detecting defect candidates by comparing based on using scatter diagrams that are obtained from the detected image and reference image is disclosed by Japanese Patents Laid-open No. 2002-168799 and No. 2003-271927.

Next, the image comparison section 110 calculates the threshold values for accepting the calculated positional displacement amount and brightness difference about each pixel of the detected image and reference image, and compares the brightness values of the detected image and reference image on the basis of the threshold values. If any pixel has a brightness difference greater than a threshold value, the image comparison section 110 extracts the pixel as a defect candidate and its partial image. In this instance, the defect candidate pixel position (detection position), brightness value, dimensions, reference image brightness, and the like are calculated as feature (characteristics) amounts as shown in FIG. 5. The threshold values used for comparison are to be set by the user as one inspection condition and automatically tuned by the threshold value setup section 111.

In the present embodiment, the image signals of chips 3 and 2 are also subjected to the same parallel process. Defect candidates found between chips 1 and 2, which are detected by defect candidate extraction unit 15-1, and defect candidates found between chips 2 and 3, which are detected by defect candidate extraction unit 15-2, are then examined to locate defect candidates whose coordinates match. An AND process (1101 in FIG. 11) is performed while the located defect candidates are handled as defect candidates of chip 2. The partial images, feature (characteristics) amounts, and positional displacement amounts of such defect candidates are transferred to the defect detection unit 16 via memory 115.

Next, the defect detection unit 16 (positional displacement re-detection section 116) performs a positional displacement detection/positional alignment process by using the images and feature amounts of the defect candidates transferred. The positional displacement detection method employed by the positional displacement re-detection section 116 can be the same as or different from that is employed by the positional displacement detection section 108. It is also possible to effect positional alignment only by using the positional displacement amount calculated by the positional displacement detection section 108 and without performing a positional displacement re-detection process.

Figure 7:
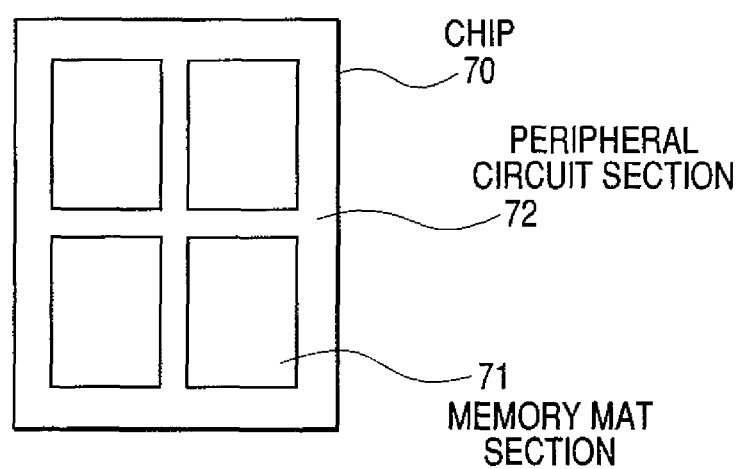
FIG. 7 shows a typical chip structure.

Next, a brightness correction process is performed (brightness re-correction section 117). It does not matter whether the employed brightness correction method is the same as that is used by the brightness correction section 109. The use of a different brightness correction method according to one embodiment of the present invention will now be described with reference to FIG. 14. First of all, step 117-1 is performed to divide the extracted reference image into a plurality of areas in accordance with the pattern. Step 117-2 is then performed to calculate the correction amounts for each area by using the statistics of pixels belonging to each area. This is the same as for dividing the reference image shown in FIG. 15A into area B (slash area in FIG. 15B) and area C (slash area in FIG. 15C), preparing their respective scatter diagrams in which the X-axis and Y-axis indicate the brightness of a partial image containing defect candidates and the brightness of its reference image, respectively, to depict the pixels within the areas, and calculating the correction amounts within each resulting scatter diagram. As regards the correction amounts for the scatter diagram for each area, a linear expression is determined, as indicated in FIGS. 15B and 15C, by least squares approximation within a scatter diagram. The gradient and y-intercept are used as the correction amounts. Although the method for dividing defect candidates according to the pattern has been described above, the method shown in FIG. 12 may alternatively be used in conjunction with the present embodiment to provide more detailed brightness corrections than indicated in FIG. 12. This makes it possible to provide corrections separately for the peripheral circuit section 72 being an area that a false-information (a false-report) tends to generate brightly and for the memory mat section 71 as shown in FIG. 7. The areas can be defined in accordance with chip design information such as CAD data, chip layout data, and chip image or in accordance with test inspection results. Further, the areas can also be automatically defined in accordance with input image information.

Next, the image re-comparison section 118 calculates the threshold values for accepting the calculated positional displacement amount and brightness difference amount for each pixel, as is the case with the image comparison section 110, and compares the brightness values of the defect candidate image and its reference image on the basis of the threshold values. If any pixel has a brightness difference greater than a threshold value, the image re-comparison section 118 extracts the pixel as a defect pixel, and calculates the feature amounts in the same manner as the image comparison section 110. It does not matter whether the threshold values used for comparison are the same as for the image comparison section 110 or individually set by the user. It is also possible to repeatedly perform the processes of sections 116 to 119 and conduct a tuning operation while viewing the detection results. An alternative is to perform automatic setup for each image. The method for performing automatic setup will be described later.

The image re-comparison section 118 also collates the positional displacement amounts and feature amounts calculated by the defect candidate extraction unit 15 with those calculated by the defect detection unit 16.

In the image re-comparison section 118, the collation of defect candidate detection results of the same location, which are calculated by the defect candidate extraction unit 15 and defect detection unit 16, will now be described in accordance with the first embodiment and with reference to FIGS. 16A1 through 16B3. FIGS. 16A1 and 16A2 respectively indicate the positional displacement amounts that are calculated as defect candidate detection results of the same location by the defect candidate extraction unit 15 and defect detection unit 16. White clear portions in the drawings represent defect areas in which the positional displacement amount is greater than the threshold value. When the positional displacement amounts of the defect image and reference image, which are calculated by the defect candidate extraction unit 15 and defect detection unit 16, differ from each other, the defect candidates shown in FIG. 16A1 are not extracted as defect areas in FIG. 16A2. In this instance, the defect candidates are not extracted as defects because it is concluded that the positional displacement amount calculated by the positional displacement detection section 108 of the defect candidate extraction unit 15 is incorrect.

FIGS. 16B1 and 16B2 respectively indicate the feature amounts that are calculated as defect candidate detection results of the same location by the defect candidate extraction unit 15 and defect detection unit 16. White clear portions in the drawings represent defect areas in which the brightness difference is greater than the threshold value. In this instance, the detection positions are collated with each other as one feature amount. If they do not match, the corresponded defect candidate is not extracted as a defect.

In the image re-comparison section 118, the collation of defect candidate detection results of the same location, which are calculated by the defect candidate extraction unit 15 and defect detection unit 16, will now be described in accordance with the second embodiment and with reference to FIGS. 17C1 and 17C2. FIG. 17C1 shows the images of chips 1 and 2, which are compared by the defect candidate extraction unit 15. It illustrates an example in which a defect candidate exists in chip 1. A case where an isolated defect in a sparse pattern area is extracted as a nonfatal defect will now be described. Whether or not a specific defect candidate is a fatal defect or nonfatal defect is determined by judging for a circuit pattern (wiring pattern, etc.) behind the defect candidate. At a stage where the defect candidate extraction unit 15 performs an image comparison process, it is unknown whether a defect candidate is contained in chip 1 or 2. In other words, it is unknown which chip provides a background image. Therefore, when the background pattern information is to be acquired, chips 1 and 2 should be both used to determine the average as shown in FIGS. 17C1 and 17C2. Consequently, the reliability is low and no accurate judgment can be formed. However, FIG. 17C2 shows the defect candidate image and its reference image, which are compared by the defect detection unit 16. At this stage, it is known whether a defect is contained in chip 1 or 2. It is therefore possible to accurately acquire the background circuit pattern information and judge whether a defect candidate is a fatal defect or nonfatal defect.

As described above, highly reliable results can be obtained when the specimen to be inspected is subjected to multi-step positional displacement detection processes, which vary in processing unit or processing method, and multi-step brightness correction processes, which vary in processing unit or processing method, and the results of such processes are collated with each other. When, for instance, a circuit pattern formed on a semiconductor wafer, which is covered with an optically transparent, flat insulation film, is to be inspected after a CMP process, the wafer image, which has been subjected to the CMP process and picked up by the detection unit 13, is affected, for instance, reflected light distribution generating by insulation film thickness variations in the wafer plane and by the roughness and fineness of pattern in chip. Therefore, the wafer image has variations in brightness depending on the wafer location. When the image, which has the variations in brightness, is subjected to multi-step brightness correction processes, defects can be revealed while the influence of inter-image brightness variations is reduced. As a result, the defect detection rate can be increased. Further, when the image obtained after the AND process is performed by the defect candidate extraction unit 15, that is the image which is performed re-processing and re-judgment by using the image whose defect position and background area are known, it is possible to acquire more accurate pattern information and form a highly reliable judgment.

Figure 18:
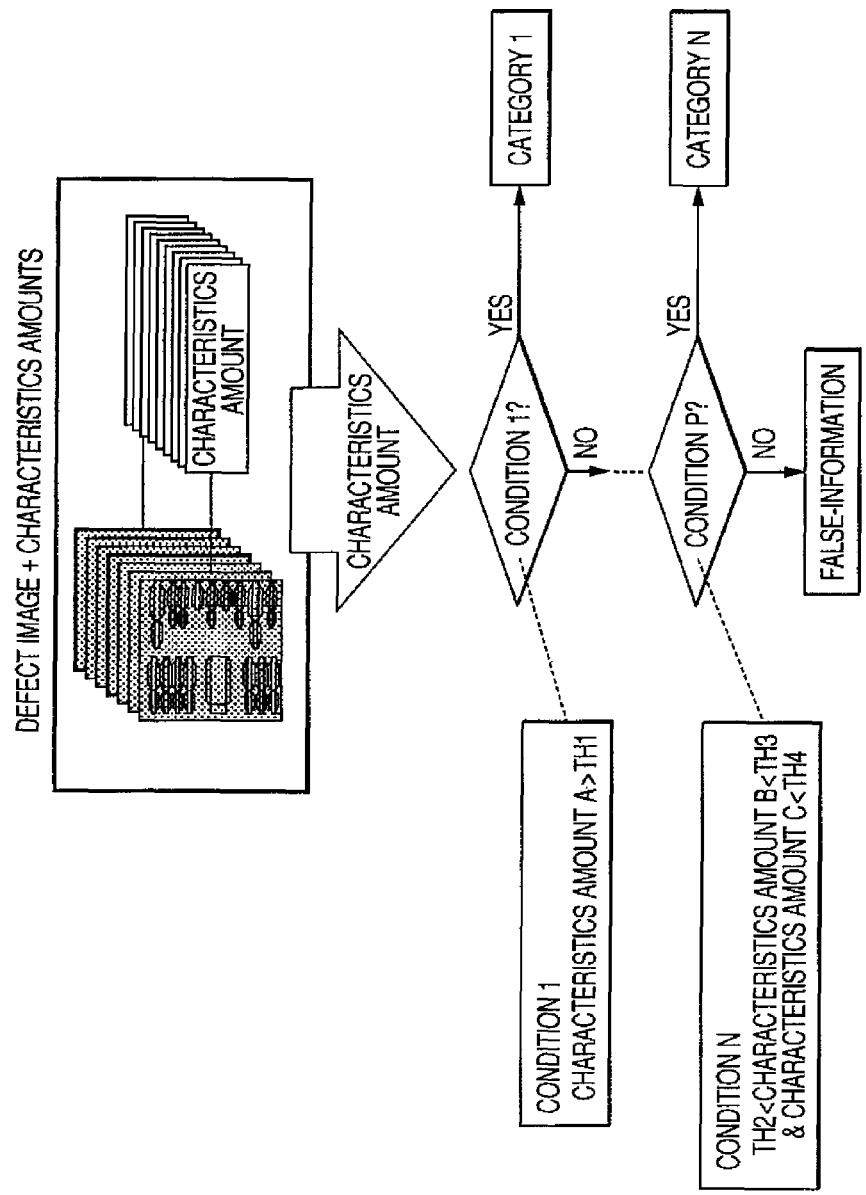
FIG. 18 illustrates how defects are classified by a defect detection unit according to one embodiment of the present invention.
Figure 19A:
FIG. 19A shows a partial image containing defect A.
Figure 19B:
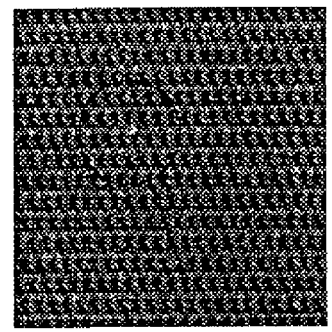
FIG. 19B shows a partial image containing defect B.
Figures 19C, 19D:
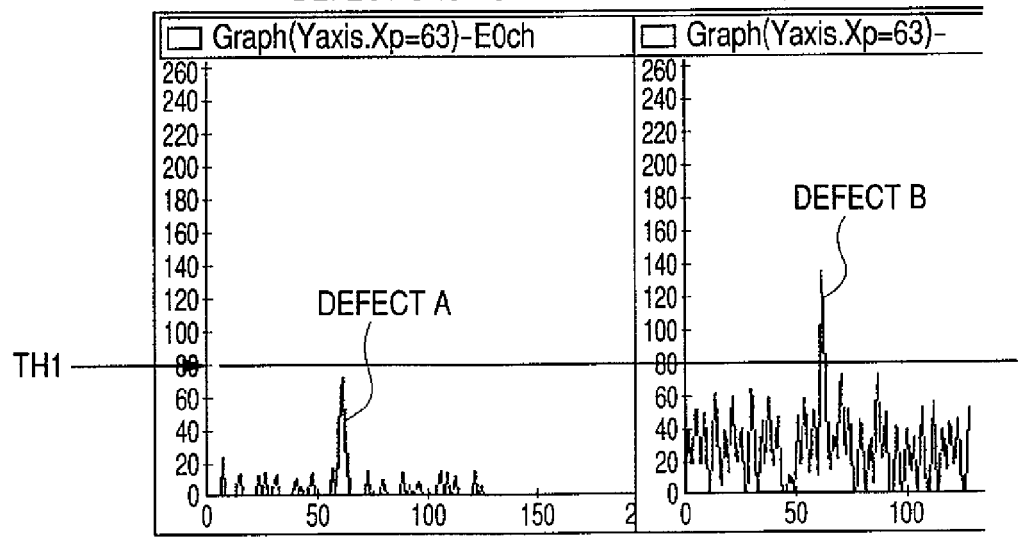
FIG. 19C shows a defect brightness waveform corresponding to FIG. 19A.
FIG. 19D shows a defect brightness waveform corresponding to FIG. 19B.

As described above, two comparison results are collated with each other to remove any false-information, and then the defect classification section 119 classifies defects into one or more categories by their feature (characteristics) amounts. One embodiment of a classification process is shown in FIG. 18. A first step is performed to check whether the feature amounts of defects, which are calculated from the defect image and reference image, meet the predefined classification conditions (hereinafter referred to as a classification rule). Defects satisfying the predefined classification conditions are then classified into one category. If there is any defect that does not fall under any category, it may be excluded and labeled as nondefective. The threshold values used with the classification rule (e.g., TH1, TH2, TH3, and TH4 in FIG. 18) are to be manually set by the user while viewing the feature amounts of each defect. An alternative is to sample a certain number of defect images and automatically calculate the statistical threshold values for use with the classification rule. Another alternative is to automatically calculate the threshold values appropriate for each defect image. FIGS. 19A and 19B illustrate the calculations of classification threshold values for each defect image. FIGS. 19A and 19B show partial images containing detected defects A and B, respectively. FIGS. 19C and 19D show defect brightness waveforms that correspond to FIGS. 19A and 19B, respectively.

FIG. 19A is dark overall. As shown in FIG. 19C, the brightness value of defect A is small. Defect B in FIG. 19B, on the other hand, has a great brightness value as shown in FIG. 19D; however, the peripheral brightness value is also great. For explanation purposes, it is assumed that the classification conditions are as indicated below:

[Classification Conditions]
  if defect brightness>TH then defect else false-information To avoid picking up background noise from an image shown in FIG. 19B, it is necessary that threshold value TH1 be greater than the background noise level (TH1 in FIGS. 19C and 19D). In such an instance, however, defect A is excluded as a false-information because it is smaller than threshold value TH1.

To solve the above problem, the present invention automatically sets by calculating the judgment conditions (inspection sensitivity) using detection and classification of defect (background conditions of reference portion (brightness, contrast, pattern density, and other feature amounts)) for each partial image containing defects or defect candidates (automatic defect classification based on floating judgment conditions (threshold value)). FIG. 20A shows the corresponded processing flowchart according to one embodiment of the present invention. First of all, step 201 is performed to set threshold value TH0, which serves as the base (for performing proper defect classification for typical or standard defect C). Threshold value TH0 may be calculated from a statistical value of defect portions on a plurality of wafers (this statistical value serves as a typical or standard defect section value) or experimentally set as a typical or standard value by the user. FIG. 20B shows an example in which threshold value TH0 is set in accordance with the image of typical or standard defect C. Next, step 202 is performed to calculate the reference brightness value (average brightness value) L of the reference portion corresponding to the typical or standard defect portion that has been used for TH0 calculation. FIG. 20C shows an example in which the reference brightness value L is calculated from the reference image (background image) of typical or standard defect C, which has been used for TH0 setup. Step 203 is then performed to calculate the brightness value M of the reference section for each defect image. FIGS. 20D and 20E show examples in which the brightness value M is calculated from the reference sections for defects A and B, which are shown in FIGS. 19A through 19D. Finally, step 204 is performed to calculate the threshold values TH for individual defects from the relationship between the reference brightness value L of the reference portion, which has been determined from an image that has been used for TH0 setup, and the brightness value M that is calculated from the reference portions of individual defects. Equation (1) is used as one embodiment of a method for determining the threshold values TH from the relationship between the values L and M.

$$TH = TH0 - (L - M) \qquad \text{Equation (1)}$$

As described above, the classification threshold values (inspection sensitivity) TH are automatically set for each defect or defect candidate image. This applies to the threshold values for various feature amounts (brightness, contrast, pattern density, etc.). A high-sensitivity inspection can then be conducted on the entire wafer surface even when the brightness greatly varies from a central chip on a semiconductor wafer to a peripheral chip.

Figure 21:
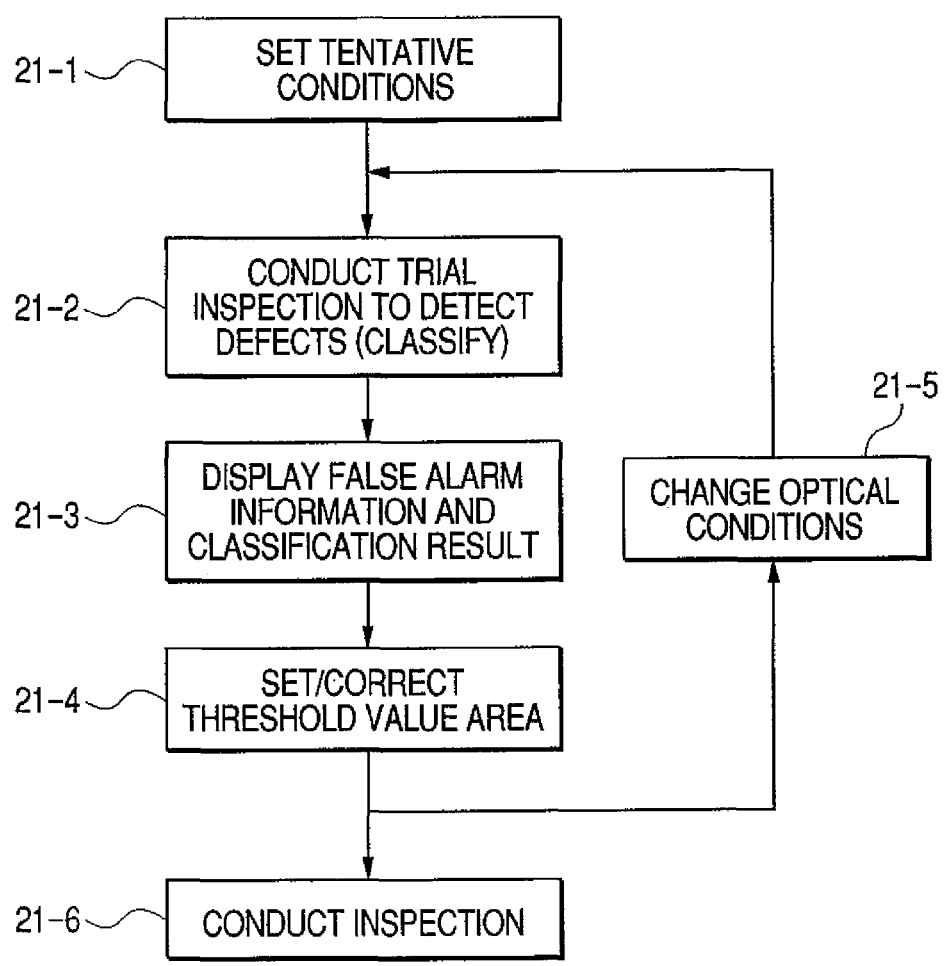
FIG. 21 illustrates how a defect detection result is reflected, for instance, in threshold values for comparison processes that are performed for defect candidate extraction and defect detection by a defect detection unit according to one embodiment of the present invention.

The defect detection results obtained by the defect detection unit 16 according to the present invention as described above are further reflected in the threshold values for the comparison process for defect candidate extraction and defect detection. Its embodiment will now be described with reference to FIG. 21. First, the user sets up general conditions (step 21-1) and conducts a trial inspection (step 21-2). The trial inspection ranges from defect candidate extraction to detection and classification of defect. Step 21-3 is then performed to display a classification result list. The displayed list indicates a false-information percentage as well as the brightness differences from the reference portions of candidates that are labeled as a false-information. While viewing the listed information, the user resets the threshold values (step 21-4) and may repeat only the defect detection process and defect classification process, which are performed by the defect detection unit 16, or repeat the defect candidate extraction process, which is performed by the defect candidate extraction unit 15, and subsequent processes. Further, it is possible to change not only the comparison process threshold values but also the optical conditions (light amount, polarization conditions, focal position, etc.) while viewing the displayed classification result list (step 21-5). The inspection conditions are then optimized to initiate an inspection (step 21-6).

Figure 22:
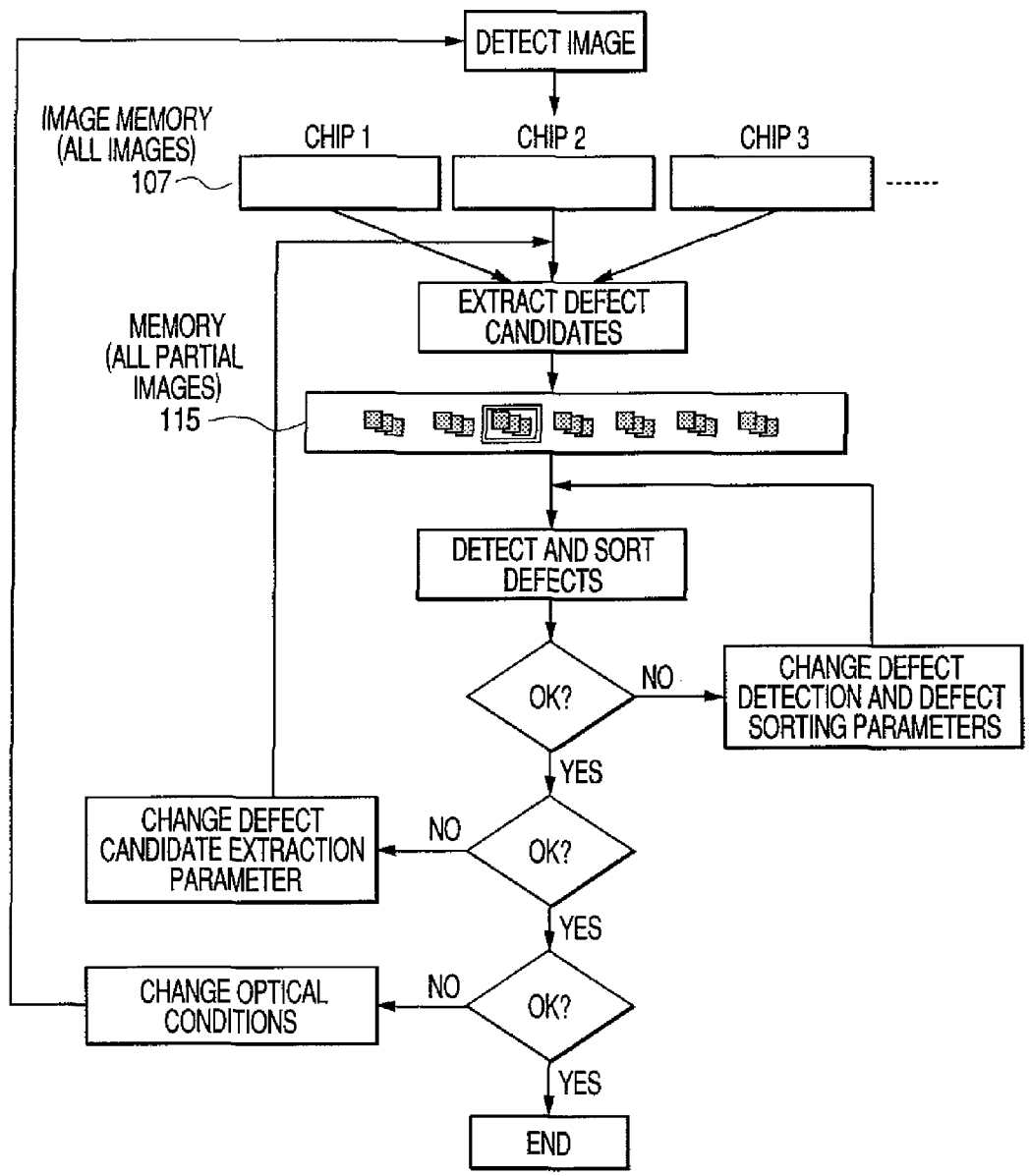
FIG. 22 is a flowchart illustrating an inspection condition optimization process that is performed in accordance with one embodiment of the present invention.

FIG. 22 is a flowchart illustrating the condition optimization process. The pattern inspection apparatus according to the present invention includes a memory 107 for storing the detected images of all chips and a memory 115 for storing a partial image containing all defect candidates and its reference image. It is therefore possible to achieve optimization by repeating the process under various defect detection/defect classification conditions. It is also possible to achieve optimization by repeating the process under various defect candidate extraction conditions. Further, the optical conditions can also be optimized based on evaluating tuned detection/classification results.

In an inspection for comparing two images and detecting defects from the differences between the compared two images, the present invention enhances the image acquisition speed by operating a plurality of units to perform parallel processing for image detection by the image sensor 104 as described above. Further, the present invention can attain an inspection speed that is equivalent or close to the image acquisition speed of the image sensor 104 by operating a plurality of units to perform parallel processing for image comparison based defect candidate extraction and operating a plurality of units to perform parallel processing for detecting defects only from defect candidates and classifying detected defects. If, for instance, the maximum image acquisition speed of the image sensor 104 is 3.2 Gpps (pps: pixels per second), an inspection speed of 3.2 Gpps can be attained by operating two parallel units as provided by the present invention even if the processing capacity of the defect candidate extraction unit 15 is half the maximum image acquisition speed, that is, 1.6 Gpps. Further, even if the image sensor's image acquisition speed is higher than mentioned above, the employed optical conditions shorten the image sensor's image accumulation time, or the image acquisition speed is otherwise increased, the resulting situation can be properly corresponded without having to increase the processing speed as far as M sets of the defect candidate extraction unit 15 and N sets of the defect detection unit 16 are used. For example, even if the image sensor's image acquisition speed is further raised up to 6.4 Gpps, the resulting situation can be properly corresponded at an image processing speed of 6.4 Gpps when four sets of the defect candidate extraction unit 15 having a processing capacity of 1.6 Gpps are operated in a parallel manner. Even if the magnification is further increased to inspect patterns that are increasingly rendered microscopic, a higher speed can be attained simply by increasing the number of image sensors and various component units to be operated in a parallel manner.

Unlike a comparative inspection in which there are inter-chip brightness differences (color differences) that are caused by various factors, including inter-chip film thickness differences, light amount differences accumulated based on irregularity of stage-speed, and illumination variations, the inspection can be performed two times by using a plurality of different methods. When a plurality of information derived from such different inspections are collated with each other to reveal feeble signal defects that are hidden behind intense brightness irregularities, high inspection reliability and sensitivity can be achieved.

Figure 23:
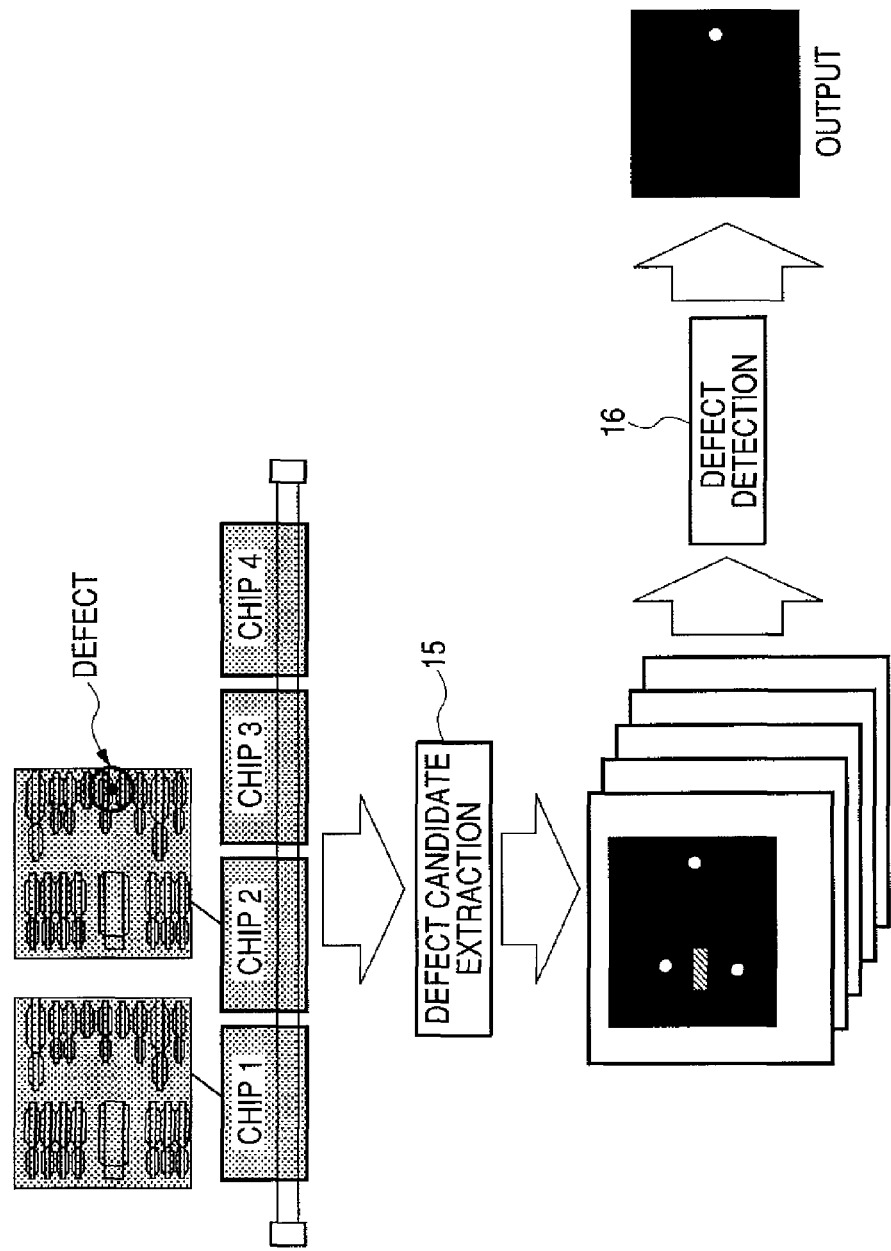
FIG. 23 illustrates one embodiment according to the present invention in which an inspection process is performed two times by different methods to collate the obtained two sets of information and reveal hidden defects indicated by feeble signals.

Thereby, as shown in FIG. 23, a high-speed, high-sensitivity comparative inspection can then be conducted by allowing the defect candidate extraction unit 15 to perform a high-sensitivity with a lower threshold value and rough high-speed inspection for the images of all chips, and to narrow down the target area from all chips by extracting partial images of many defect candidates including false-information, and allowing the defect detection unit 16 to perform a detailed inspection/ classification (defect detection/defect classification) process within the resulting narrowed limited area.

The processes performed by the defect candidate extraction unit 15 and defect detection unit 16 according to the present invention, which have been described above, are implemented by allowing the CPU to perform software processing. However, the core of computations such as normalized correlation computation and feature space formation may alternatively be performed by hardware such as an LSI. The processing speed can be further increased by the use of such hardware. Further, the present invention can detect defects ranging in size from 10 nm to 90 nm even if the difference in large brightness is between the dies to be compared due to delicate differences in the pattern film thickness after smoothing process such as CMP etc. and due to the use of short-wavelength illumination light.

Figure 24:
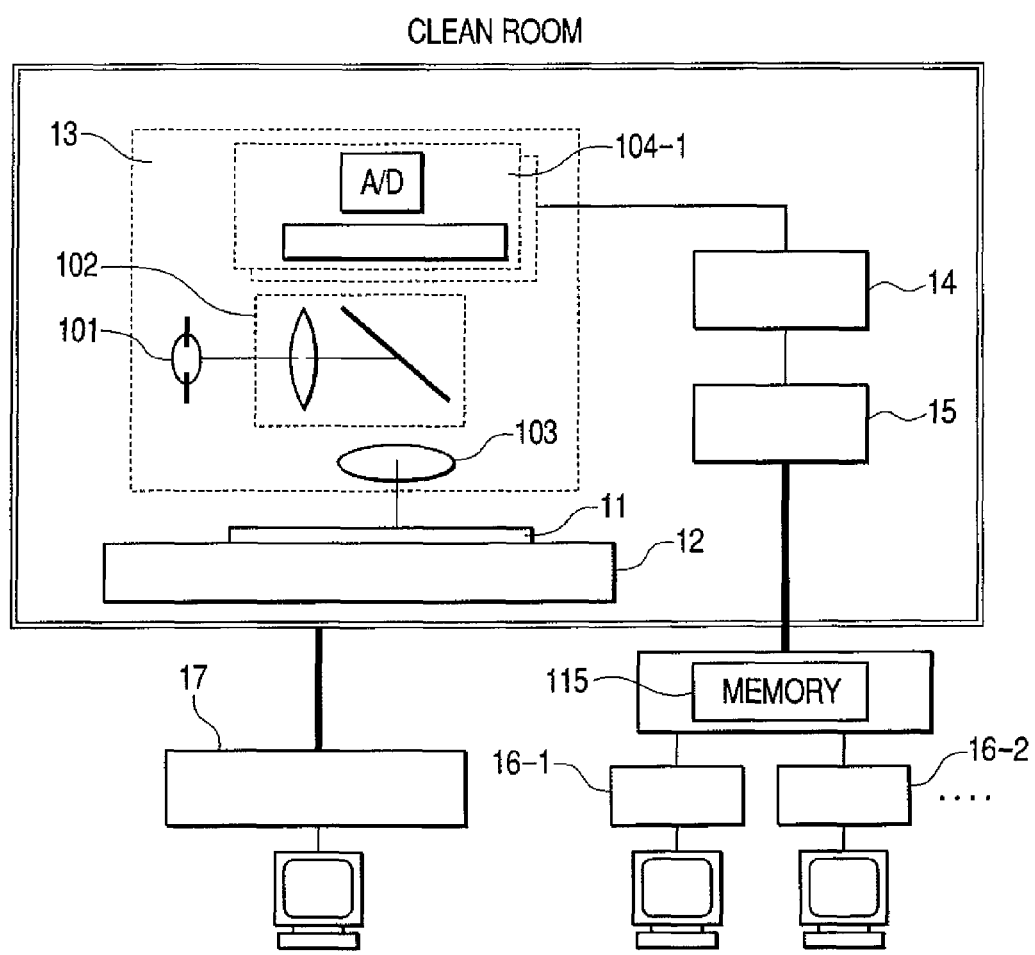
FIG. 24 illustrates the configuration of another embodiment of a pattern defect inspection apparatus according to the present invention, which differs from the one shown in FIG. 1.
Figure 25:
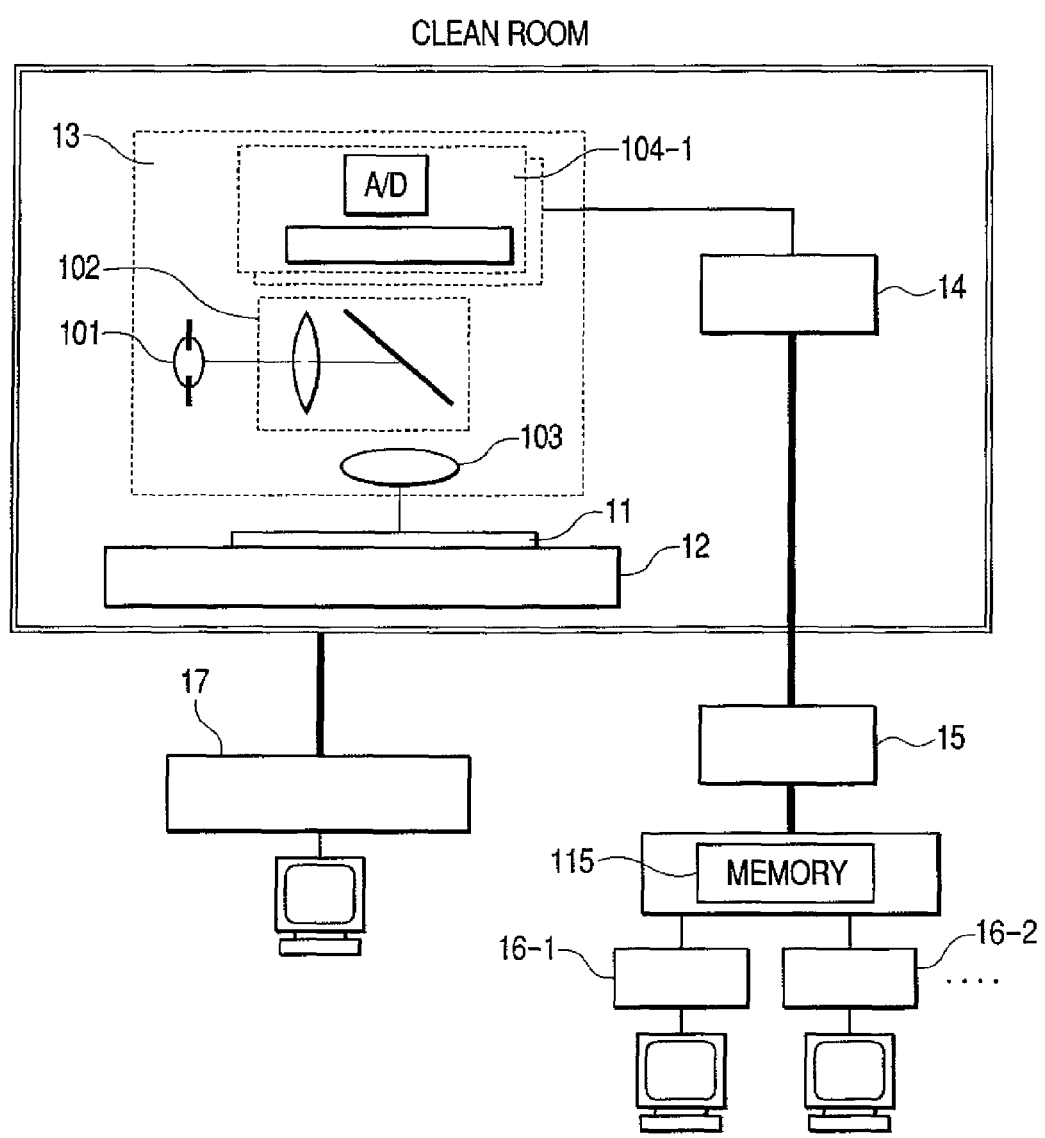
FIG. 25 illustrates the configuration of still another embodiment of a pattern defect inspection apparatus according to the present invention, which differs from those shown in FIGS. 1 and 24.

The pattern inspection apparatus according to the present invention includes a memory 107 for storing the detected images of all chips and a memory 115 for storing a partial image containing all defect candidates and its reference image. Therefore, the detection unit 13, defect candidate extraction unit 15, and defect detection unit 16 operate asynchronously with each other and can be separately installed. In a clean room where a semiconductor inspection is conducted as indicated in FIG. 24, for example, only the stage 12, detection unit 13, and defect candidate extraction unit 15 may be installed so that the defect detection unit 16 installed outside the clean room performs a defect detection/defect classification process off-line. Alternatively, only the stage 12 and detection unit 13 may be installed in the clean room as indicated in FIG. 25 so as to perform the subsequent processes off-line outside the clean room. Another alternative is to detect the image of one specimen in a parallel manner while tuning the defect candidate extraction, defect detection, and defect classification process conditions for another specimen.

Figure 26:
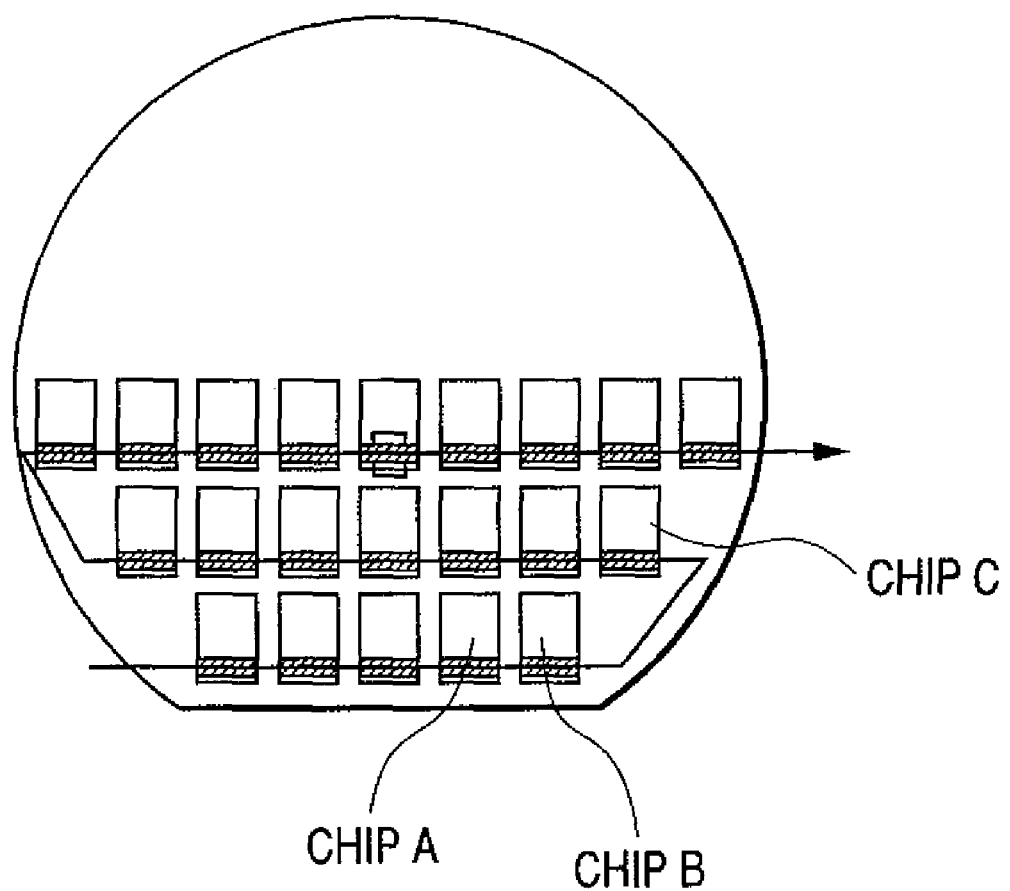
FIG. 26 illustrates a chip comparison method according to the present invention.

The chip comparison method according to the present invention is such that chip B, which is at a wafer edge (periphery), is first compared with chip A and then compared with chip C as shown in FIG. 26 to perform an AND operation on the comparison results. Therefore, chips at a wafer edge can also be inspected.

The comparative inspection apparatus according to the present invention can perform an inter-cell comparative inspection while conducting an inter-chip comparative inspection.

When a low-k film inspection is conducted on a $SiO_2$ film, SiOF film, BSG film, SiOB film, porous silica film, or other inorganic insulation film or methyl-$SiO_2$ film, MSQ film, polyimide film, parylene film, amorphous carbon film, or other organic insulation film, the pattern inspection method according to the present invention can detect defects ranging in size from 20 nm to 90 nm no matter whether any local brightness difference is caused by in-film refractive index distribution variation.

One embodiment of the present invention has been described with reference to comparative inspection images handled by an optical visual inspection apparatus that inspects semiconductor wafers. However, the present invention can also be applied to comparative images for electron-beam pattern inspection. Further, the inspection target (the sample) is not limited to semiconductor wafers. For example, the present invention can also be applied to TFT substrates, photomasks, and printed circuit boards as far as defects are inspected for by comparing images.

The present embodiment, which has been described above, performs parallel processing for image comparison purposes and attains an inspection speed that corresponds to the processing speed, which depends, for instance, on the image sensor's image acquisition speed, image accumulation time, and scanning width.

Even when the same pattern in different images varies in brightness because, for instance, the film thickness of the semiconductor wafer to be inspected varies, the amount of illumination light varies, the image sensor sensitivity varies from one pixel to another, or the light amount accumulation time varies, the present embodiment prevents false-information from being generated by such brightness variations and properly detects defects.

The images to be compared vary in brightness due, for instance, to inter-chip brightness differences (color irregularities), which arise, for instance, out of inter-chip film thickness differences, inter-pixel image sensor sensitivity differences, accumulated light amount differences caused by stage speed irregularities, and illumination variations. In such a circumstance, the present embodiment adjusts the image brightness with a plurality of different frequencies to reveal and detect feeble signal defects, which are hidden behind intense brightness irregularities.

The present embodiment can set a threshold value in accordance with intra-wafer coordinates and intra-chip coordinates. The inspection sensitivity can then be automatically optimized at various locations. Therefore, a high-sensitivity inspection can be conducted. In this instance, the chip design information and threshold value setting area can be superposed on each other when displayed. This makes it easy to confirm or correct the threshold value setting area or otherwise adjust the sensitivity.

The invention may be embodied in other specific forms without departing from the spirit of essential feature thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for inspecting pattern defects, the apparatus comprising:
   an image acquisition unit which acquires an image of a specimen;
   a defect candidate extraction unit configured to perform a defect candidate extraction process by comparing a detected image signal with a reference image signal; and
   a defect detection unit configured to perform a defect detection process and a defect classification process based on a partial image containing a defect candidate that is extracted by said defect candidate extraction unit,
   wherein said image acquisition unit and said defect candidate extraction unit work asynchronously with each other, and
   said defect detection unit includes plural defect detectors, each of the plural defect detectors performs the defect detection process and the defect classification process in parallel based on partial images which are different with each other.

2. An apparatus according to claim 1, wherein said plural defect detectors detect defects from differing pairs of images from each other.

3. An apparatus according to claim 1, wherein said plural defect detectors detect defects from differing pairs of specimens from each other.

4. An apparatus for inspecting defects, comprising:
an image acquisition unit which acquires an optical image of a specimen with an image sensor and output an image signal;
a defect candidate extraction unit which processes the image signal output from the image sensor to extract defect candidates from the image signal;
a defect detection unit which detects defects from the defect candidates extracted by said defect candidate extraction unit; and
a display unit which displays information about the defects detected by said defect detection unit,
wherein said image acquisition unit and said defect detection unit work asynchronously with each other, and
said defect detection unit includes plural defect detectors operating concurrently, performing the defect detection process and a defect classification process based on partial images which are different with each other.

5. An apparatus according to claim 4, wherein said defect detection unit further classifies said detected defects into plural defect classes.

6. An apparatus according to claim 4, wherein said image acquisition unit including a light source which emits a light, an illumination optical part which illuminate the specimen with the light emitted from the light source and a light collecting part which collects light from the specimen illuminated by the illumination optical part.

7. An apparatus according to claim 4, wherein said image sensor of said image acquisition unit is a TDI image sensor.

8. An apparatus according to claim 4, wherein said plural defect detectors detect defects from differing pairs of images from each other.

9. An apparatus according to claim 4, wherein said plural defect detectors detect defects from differing pairs of specimens from each other.

10. A method of inspecting defects, comprising:
acquiring an image of a specimen with an image sensor and outputting an image signal;
processing the image signal output from the image sensor and extracting defect candidates from the image signal;
detecting defects from the extracted defect candidates; and
displaying information about the detected defects,
wherein the acquiring the image and the detecting defects are performed asynchronously with each other, and
in the detecting defects, plural defect detectors are used, and each of the plural defect detectors performs a defect detection process and a defect classification process in parallel based on partial images which are different with each other.

11. A method according to claim 10, wherein the detecting defects, further including classifying said detected defects into plural defect classes.

12. A method according to claim 10, wherein the acquiring the image including, emitting a light from a light source, illuminating the specimen with the light and collecting light from the specimen illuminated by the light emitted from the light source.

13. A method according to claim 10, wherein said image sensor is a TDI image sensor.

14. A method according to claim 10, wherein said plural defect detectors detect defects from differing pairs of images from each other.

15. A method according to claim 10, wherein said plural defect detectors detect defects from differing pairs of specimens from each other.

16. An apparatus for inspecting defects, comprising:
an image acquisition unit which acquires with an image sensor an image of a specimen illuminated with light and outputs an image signal;
an image processor unit which processes the image signal output from the image acquisition unit; and
a display unit which displays information processed by the image processor unit,
wherein said image acquisition unit and said image processor unit work asynchronously with each other, and
said image processor unit includes plural defect detectors, each of the plural defect detectors performs a defect detection process and a defect classification process in parallel based on partial images which are different with each other.

17. An apparatus according to claim 16, wherein said image processor unit including a defect candidate extraction part which processes the image signal output from the image acquisition unit to extract defect candidates and a defect detection part which detects defects from the defect candidates extracted by said defect candidate extraction part.

18. An apparatus according to claim 17, wherein said defect detection part further classifies said detected defects into plural defect classes.

19. An apparatus according to claim 16, wherein said image acquisition unit including a light source which emits a light, an illumination optical part which illuminate the specimen with the light emitted from the light source and a light collecting part which collects light from the specimen illuminated by the illumination optical part.

20. An apparatus according to claim 16, wherein said image sensor of said image acquisition unit is a TIDI image sensor.

21. An apparatus according to claim 16, wherein said plural defect detectors detect defects from differing pairs of images from each other.

22. An apparatus according to claim 16, wherein said plural defect detectors detect defects from differing pairs of specimens from each other.

23. A method for inspecting defects, comprising:
acquiring an image of a specimen with an image sensor and outputting an image signal;
processing the output image signal to detect defects; and
displaying information relating to the detected defects on a display screen,
wherein the acquiring the image and the processing the output image signal are preformed asynchronously with each other, and
the processing the output image signal uses plural defect detectors, each of the plural defect detectors performs a defect detection process and a defect classification process in parallel based on partial images which are different with each other.

24. A method according to claim 23, wherein the processing includes a defect candidate extraction sub-operation for extracting defect candidates from the image signal acquired by the acquiring, and a defect detection sub-operation for detecting defects from the defect candidates extracted by said defect candidate extraction sub-operation.

25. A method according to claim 24, wherein in the defect detection, sub-operation, further including a sub-operation of classifying said detected defects into plural defect classes.

26. A method according to claim 23, wherein in the acquiring, the image includes sub-operations of emitting a light, illuminating the specimen with the emitted light and collecting light from the specimen illuminated by the emitted light.

27. A method according to claim 23, wherein in the acquiring the image, said image is acquired with a TDI image sensor.

28. An apparatus according to claim 23, wherein said plural defect detectors detect defects from differing pairs of images from each other.

29. An apparatus according to claim 23, wherein said plural defect detectors detect defects from differing pairs of specimens from each other.

* * * * *